United States Patent
Page et al.

(10) Patent No.: US 9,546,362 B2
(45) Date of Patent: Jan. 17, 2017

(54) GENES AND PROTEINS FOR ALKANOYL-COA SYNTHESIS

(75) Inventors: Jonathan E. Page, Saskatoon (CA); Jason M. Stout, Saskatoon (CA)

(73) Assignees: National Research Council of Canada, Ottawa (CA); University of Saskatchewan, Saskatoon (CA)

( * ) Notice: Subject to any disclaimer, the term of this patent is extended or adjusted under 35 U.S.C. 154(b) by 0 days.

(21) Appl. No.: 14/232,465

(22) PCT Filed: Jul. 13, 2012

(86) PCT No.: PCT/CA2012/000656
§ 371 (c)(1),
(2), (4) Date: Jan. 13, 2014

(87) PCT Pub. No.: WO2013/006953
PCT Pub. Date: Jan. 17, 2013

(65) Prior Publication Data
US 2014/0141476 A1    May 22, 2014

Related U.S. Application Data

(60) Provisional application No. 61/507,331, filed on Jul. 13, 2011.

(51) Int. Cl.
| | | |
|---|---|---|
| C12N 9/00 | (2006.01) | |
| C12N 9/10 | (2006.01) | |
| C12N 9/90 | (2006.01) | |
| C12N 15/82 | (2006.01) | |
| C12P 7/42 | (2006.01) | |
| C12P 17/06 | (2006.01) | |

(52) U.S. Cl.
CPC . *C12N 9/93* (2013.01); *C12N 9/00* (2013.01); *C12N 9/1029* (2013.01); *C12N 9/90* (2013.01); *C12N 15/8243* (2013.01); *C12P 7/42* (2013.01); *C12P 17/06* (2013.01); *Y02P 20/52* (2015.11)

(58) Field of Classification Search
CPC ...... C12N 15/8243; C12N 9/00; C12N 9/0036
See application file for complete search history.

(56) References Cited

U.S. PATENT DOCUMENTS

2006/0035236 A1    2/2006 Keim et al.

FOREIGN PATENT DOCUMENTS

| JP | 2000078979 A | 3/2000 |
| JP | 2001029082 A | 2/2001 |
| JP | 2007020466 A | 2/2007 |
| WO | 9824929 A1 | 6/1998 |
| WO | 2011017798 A1 | 2/2011 |

OTHER PUBLICATIONS

Stout et al. (The hexanoyl-CoA precursor for cannabinoid biosynthesis is formed by an acyl-activating enzyme in Cannabis sativa trichomes. The Plant Journal, vol. 71, Issue 3 Aug. 2012 pp. 353-365).*

Sparkes, Imogen A. et al. Rapid, transient expression of fluorescent fusion proteins in tobacco plants and generation of stably transformed plants. Nature Protocols, vol. 1, No. 4, pp. 21019-22025, 2006.

Alvarez JP, et al. Endogenous and synthetic microRNAs stimulate simultaneous, efficient, and localized regulation of multiple targets in diverse species. Plant Cell 18:1134-51, 2006.

Datla R. et al. Plant promoters for transgene expression. Biotechnology Annual Review 3: 269-296, 1997.

Deblock M. et al. Transformation of *Brassica napus* and *Brassica oleracea* using Agrobacterium tumefaciens and the expression of the bar and neo genes in the transgenic plants. Plant Physiol. 91: 694-701, 1989.

Depicker A. and Montagu MV. Post-transcriptional gene silencing in plants. Curr Opin Cell Biol. 9: 373-82, 1997.

Earley, K.W. et al. Gateway-compatible vectors for plant functional genomics and proteomics. Plant J. 45, 616-629, 2006.

Fernandez-Valverde M. et al. Purification of Pseudomonas putida acyl coenzyme A ligase active with a range of aliphatic and aromatic substrates. Applied Environmental Microbiology 59:1149-1154, 1993.

Helliwell CA and Waterhouse PM. Constructs and methods for hairpin RNA-mediated gene silencing in plants. Methods Enzymology 392:24-35, 2005.

Henikoff S. et al. Tilling. Traditional mutagenesis meets functional genomics. Plant Physiol 135:630-6, 2004.

Katavic V. et al. In planta transformation of *Arabidopsis thaliana*. Mol. Gen. Genet. 245: 363-370, 1994.

Li X. et al. Deleteagene: a fast neutron deletion mutagenesis-based gene knockout system for plants. Comp Funct Genomics. 3: 158-60, 2002.

Meyer P. Understanding and controlling transgene expression. Trends in Biotechnology 13: 332-337, 1995.

Moloney MM. et al. High efficiency transformation of *Brassica napus* using Agrobacterium vectors. Plant Cell Rep. 8: 238-242, 1989.

Nelson, B.K. et al. A multicolored set of in vivo organelle markers for co-localization studies in Arabidopsis and other plants. Plant J. 51, 1126-1136, 2007.

Page J. and Nagel J. Biosynthesis of terpenophenolics in hop and cannabis. In JT Romeo, ed, Integrative Plant Biochemistry, vol. 40. Elsevier, Oxford, pp. 179-210, 2006.

Potrykus I. Gene transfer to plants: Assessment of published approaches and results. Annu. Rev. Plant Physiol. Plant Mol. Biol. 42: 205-225,1991.

(Continued)

*Primary Examiner* — Kagnew H Gebreyesus
(74) *Attorney, Agent, or Firm* — Bereskin & Parr LLP; Carmela De Luca

(57) ABSTRACT

Polypeptides having alkanoyl-CoA activity have been identified and characterized, as have nucleic acids encoding these polypeptides. Expression or over-expression of the nucleic acids alters levels of cannabinoid compounds in organisms. The polypeptides may be used in vivo or in vitro to produce cannabinoid compounds.

11 Claims, 6 Drawing Sheets

(56) References Cited

OTHER PUBLICATIONS

Rhodes CA. et al. Genetically transformed maize plants from protoplasts. Science 240: 204-207, 1988.

Shoyama Y. et al. Biosynthesis of propyl cannabinoid acid and its biosynthetic relationship with pentyl and methyl cannabinoid acids. Phytochemistry, vol. 23, Issue 9, Aug. 21, 1984, pp. 1909-1912 (abstract only).

Schwab R. et al. Highly Specific Gene Silencing by Artificial MicroRNAs in Arabidopsis. The Plant Cell, vol. 18, 1121-1133, May 2006.

Schneider K et al. A new type of peroxisomal acyl-coenzyme A synthetase from *Arabidopsis thaliana* has the catalytic capacity to activate biosynthetic precursors of jasmonic acid. The Journal of Biological Chemistry, 280:13962-72, 2005.

Songstad DD. et al. Advances in alternative DNA delivery techniques. Plant Cell Tissue Organ Cult. 40:1-15, 1995.

Stam M. et al. Distinct features of post-transcriptional gene silencing by antisense transgenes in single copy and inverted T-DNA repeat loci. Plant J. 21:27-42, 2000.

Vasil I K. Molecular improvement of cereals. Plant Mol. Biol. 25: 925-937, 1994.

Walden R. and Wingender R. Gene-transfer and plant regeneration techniques. Trends in Biotechnology 13: 324-331, 1995.

Ware MA et al. Smoked cannabis for chronic neuropathic pain: a randomized controlled trial. Canadian Medical Association Journal 182:E694-701, 2010.

Shockey J. and Browse J. Genome-level and biochemical diversity of the acyl-activating enzyme superfamily in plants. The Plant Journal 66:143-60, 2011.

Shockey JM. et al. Arabidopsis contains a large superfamily of acyl-activating enzymes. Phylogenetic and biochemical analysis reveals a new class of acyl-coenzyme a synthetases. Plant Physiology 132:1065-76, 2003.

Fernandez-Valverde M. et al. Use of long-chain fatty acid-CoA ligase (AMP-forming) from Pseudomonas fragi for the "in vitro" synthesis of natural penicillins. FEMS Microbiology Letters 96:111-114, 1992 (abstract only).

Chan A. et al. GenBank Accession No. XM_002511961, Aug. 6, 2009. Ricinus communis acetyl-CoA synthetase, putative, mRNA. Retrieved on Aug. 7, 2012 from GenBank Accession No. XM_002511961, version XM_002511961.1 gi:255541885 <http://www.ncbi.nlm.nih.gov/nucleotide/XM_002511961>.

Beuning L. et al. GenBank Accession No. ES790087, Jun. 26, 2007. 061124AALA001303CT (AALA) Royal Gala 150 DAFB fruit cortex *Malus* x *domestica* cDNA clone AALAA00130, mRNA sequence. Retrieved on Oct. 4, 2012 from GenBank Accession No. ES790087, version ES790087 GI: 149780311 <http://www.ncbi.nlm.nih.gov/nucest/ES790087>.

Pakula A.A, Sauer R.T., Genetic analysis of protein stability and functions, Annual Review of Genetics, 1989, vol. 23, pp. 289-310.

\* cited by examiner

GENES AND PROTEINS FOR ALKANOYL-COA SYNTHESIS

CROSS-REFERENCE TO RELATED APPLICATIONS

This application is a national entry of International Patent Application PCT/CA2012/000656 filed Jul. 13, 2012 and claims the benefit of U.S. Provisional Patent application Ser. No. 61/507,331 filed Jul. 13, 2011, the entire contents of both of which are herein incorporated by reference.

FIELD OF THE INVENTION

The present invention relates to nucleic acid molecules and proteins involved in the synthesis of alkanoyl-CoA thioesters, and to uses of the nucleic acid molecules and proteins for engineering cannabinoid biosynthesis in plants, micro-organisms or in cell-free systems and for creating cannabis plants with enhanced or reduced cannabinoid content.

BACKGROUND OF THE INVENTION

Cannabis sativa L. (cannabis, hemp, marijuana) is one of the oldest and most versatile domesticated plants, which today finds use as source of medicinal, food, cosmetic and industrial products. It is also well known for its use as an illicit drug owing to its content of psychoactive cannabinoids (e.g. $\Delta^9$-tetrahydrocannabinol, $\Delta^9$-THC). Cannabinoids and other drugs that act through mammalian cannabinoid receptors are being explored for the treatment of diverse conditions such as chronic pain, multiple sclerosis and epilepsy.

Cannabinoids have their biosynthetic origins in both polyketide and terpenoid metabolism and are termed terpenophenolics or prenylated polyketides (Page J., Nagel J. (2006) Biosynthesis of terpenophenolics in hop and cannabis. In J T Romeo, ed, Integrative Plant Biochemistry, Vol. 40. Elsevier, Oxford, pp 179-210.). Cannabinoid biosynthesis occurs primarily in glandular trichomes that cover female flowers at a high density. Cannabinoids are formed by a three-step biosynthetic process: polyketide formation, aromatic prenylation and cyclization (see FIG. 1).

The first enzymatic step in cannabinoid biosynthesis is the formation of olivetolic acid by a polyketide synthase enzyme that catalyzes the condensation of hexanoyl-coenzyme A (CoA) with three molecules of malonyl-CoA. The major cannabinoids, including $\Delta^9$-tetrahydrocannabinolic acid and cannabidiolic acid, are formed from the precursor hexanoyl-CoA, which is a medium chain fatty acyl-CoA (see FIG. 1). Other cannabinoids with variant side-chains are formed from aliphatic-CoAs of different lengths (e.g. $\Delta^9$-tetrahydrocannabivarinic acid is formed from an n-butyryl-CoA primer).

Hexanoyl-CoA and other acyl-CoA thioesters in plants are synthesized by acyl-activating enzymes (AAEs, also called acyl-CoA synthetases) that catalyze the activation of carboxylic acid substrates using ATP. These enzymes act on a variety of carboxylate acids including short-, medium-, long- and very long-chain fatty acids, jasmonate precursors, phenylpropanoid-derived acids (e.g. cinnamic acid) and other organic acids such as malonate, acetate and citrate. Very few medium-chain acyl CoA synthetases have been previously identified in nature. In plants, three enzymes from A. thaliana, AAE7, At4g05160 and At5g63380 have been shown to form hexanoyl-CoA from hexanoate (Schneider K et al. (2005) A new type of peroxisomal acyl-coenzyme A synthetase from Arabidopsis thaliana has the catalytic capacity to activate biosynthetic precursors of jasmonic acid. The Journal of Biological Chemistry 280: 13962-72; Shockey J M, Fulda M S, Browse J (2003) Arabidopsis contains a large superfamily of acyl-activating enzymes. Phylogenetic and biochemical analysis reveals a new class of acyl-coenzyme a synthetases. Plant Physiology 132:1065-76.) Acyl-CoA synthetases from Pseudomonas spp. have been shown to act on medium-chain fatty acids such as hexanoate (Fernandez-Valverde M, Reglero A, Martinez-Blanco H, Luengo J M (1993) Purification of Pseudomonas putida acyl coenzyme A ligase active with a range of aliphatic and aromatic substrates. Applied Environmental Microbiology 59:1149-1154.)

Cannabinoids are valuable natural products. Genes encoding enzymes involved in cannabinoid biosynthesis will be useful in metabolic engineering of cannabis to produce plants that contain very low levels, or zero levels, of THCA and other cannabinoids via targeted mutagenesis (e.g. TILLING) or other gene knockout techniques. Such genes may also prove useful for creation, via marker-assisted selection, of specific cannabis varieties for the production of cannabinoid-based pharmaceuticals, or for reconstituting cannabinoid biosynthesis in heterologous organisms such as bacteria or yeast, or for producing cannabinoids in cell-free systems that utilize recombinant proteins.

Genes encoding enzymes of cannabinoid biosynthesis can also be useful in synthesis of cannabinoid analogs and synthesis of analogs of cannabinoid precursors. Cannabinoid analogs have been previously synthesized and may be useful as pharmaceutical products.

There remains a need in the art to identify enzymes, and nucleotide sequences encoding such enzymes, that are involved in the synthesis of aromatic polyketides.

SUMMARY OF THE INVENTION

Two novel genes from cannabis have now been found which encode previously unknown alkanoyl-CoA synthetases. These two new alkanoyl Co-A synthetases are referred to herein as Cannabis sativa hexanoyl-CoA synthetase 1 (CsHCS1) and Cannabis sativa hexanoyl-CoA synthetase 2 (CsHCS2).

Thus, in a first aspect of the invention, there is provided an isolated or purified nucleic acid molecule comprising a nucleotide sequence having at least 75% sequence identity to SEQ ID NO: 1, or a codon degenerate sequence thereof.

In a second aspect of the invention, there is provided an isolated or purified nucleic acid molecule comprising a nucleotide sequence having at least 75% sequence identity to SEQ ID NO: 3, or a codon degenerate sequence thereof.

In a third aspect of the invention, there is provided an isolated or purified polypeptide comprising an amino acid sequence having at least 85% sequence identity to SEQ ID NO: 2, or a conservatively substituted amino acid sequence thereof.

In a fourth aspect of the invention, there is provided an isolated or purified polypeptide comprising an amino acid sequence having at least 85% sequence identity to SEQ ID NO: 4, or a conservatively substituted amino acid sequence thereof.

In a fifth aspect of the invention, there is provided a vector, construct or expression system comprising a nucleic acid molecule of the invention.

In a sixth aspect of the invention, there is provided a host cell transformed with a nucleic acid molecule of the invention.

In a seventh aspect of the invention, there is provided a process of synthesizing an alkanoyl-CoA in presence of an enzyme of the invention.

In an eighth aspect of the invention, there is provided a process of altering levels of cannabinoid compounds in an organism, cell or tissue comprising using a nucleic acid molecule of the present invention, or a part thereof, to silence in the organism, cell or tissue a gene that encodes an enzyme that catalyzes synthesis of an alkanoyl-CoA.

In an ninth aspect of the invention, there is provided a process of altering levels of cannabinoid compounds in an organism, cell or tissue comprising mutating genes in the organism, cell or tissue, and using a nucleic acid molecule of the present invention to select for organisms, cells or tissues containing mutants or variants of a gene that encodes an enzyme that catalyzes synthesis of an alkanoyl-CoA.

In a tenth aspect of the invention, there is provided a process of altering levels of cannabinoid compounds in an organism, cell or tissue comprising expressing or over-expressing a nucleic acid molecule of the invention in the organism, cell or tissue in comparison to a similar variety of organism, cell or tissue grown under similar conditions but without the expressing or over-expressing of the nucleic acid molecule.

In an eleventh aspect of the invention, there is provided a process of altering levels of cannabinoid compounds in an organism, cell or tissue comprising expressing or over-expressing a nucleic acid molecule encoding a polypeptide of the invention in the organism, cell or tissue in comparison to a similar variety of organism, cell or tissue grown under similar conditions but without the expressing or over-expressing of the nucleic acid molecule.

In a twelfth aspect of the invention, there is provided a process of synthesizing a naturally-occurring cannabinoid compound or a non-naturally occurring analog of a cannabinoid compound in an organism, cell or tissue comprising expressing a nucleic acid molecule of the invention in the organism, cell or tissue in the presence of a carboxylic acid and CoA.

In a thirteenth aspect of the present invention, there is provided a process of synthesizing an alkanoyl-CoA in an in vitro cell-free reaction, said process comprising: reacting a carboxylic acid with coenzyme A presence of an enzyme of the invention.

Polypeptides that are enzymes catalyzing the synthesis of alkanoyl-CoA, and nucleotide sequences encoding such enzymes, have now been identified and characterized. The nucleotide sequences may be used to create, through breeding, selection or genetic engineering, *cannabis* plants that overproduce or under-produce cannabinoid compounds, analogs of cannabinoid compounds or mixtures thereof. These nucleotide sequences may also be used, alone or in combination with genes encoding other steps in cannabinoid synthesis pathways, to engineer cannabinoid biosynthesis in other plants or in microorganisms (e.g. yeast, bacteria, fungi) or other prokaryotic or eukaryotic organisms or in cell-free systems. In addition, blocking or reducing the expression of these genes in *cannabis* could be used to block cannabinoid biosynthesis and thereby reduce production of cannabinoids.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which:

FIGS. 2A and 2B depict the retention time of an authentic hexanoyl-CoA standard. FIG. 2C depicts an assay of CsHCS1 protein, CoA, $MgCl_2$, sodium hexanoate, ATP, and HEPES buffer, in which hexanoyl-CoA was produced and detected. FIG. 2D depicts an assay of CsHCS2 protein, CoA, $MgCl_2$, sodium hexanoate, ATP, and HEPES buffer, in which hexanoyl-CoA was produced. FIG. 2E depicts an assay in which CsHCS1 protein had been previously inactivated by boiling at 95° C. for 15 minutes, CoA, sodium hexanoate, ATP, and HEPES buffer, in which no hexanoyl-CoA was produced. FIG. 2F depicts an assay in which CsHCS2 protein had been previously inactivated by boiling at 95° C. for 15 minutes, CoA, sodium hexanoate, ATP, and HEPES buffer, in which no hexanoyl-CoA was produced.

FIG. 3 depicts two graphs illustrating carboxylic acid substrates utilized by the enzymes of the invention.

DESCRIPTION OF PREFERRED EMBODIMENTS

Figure 1:
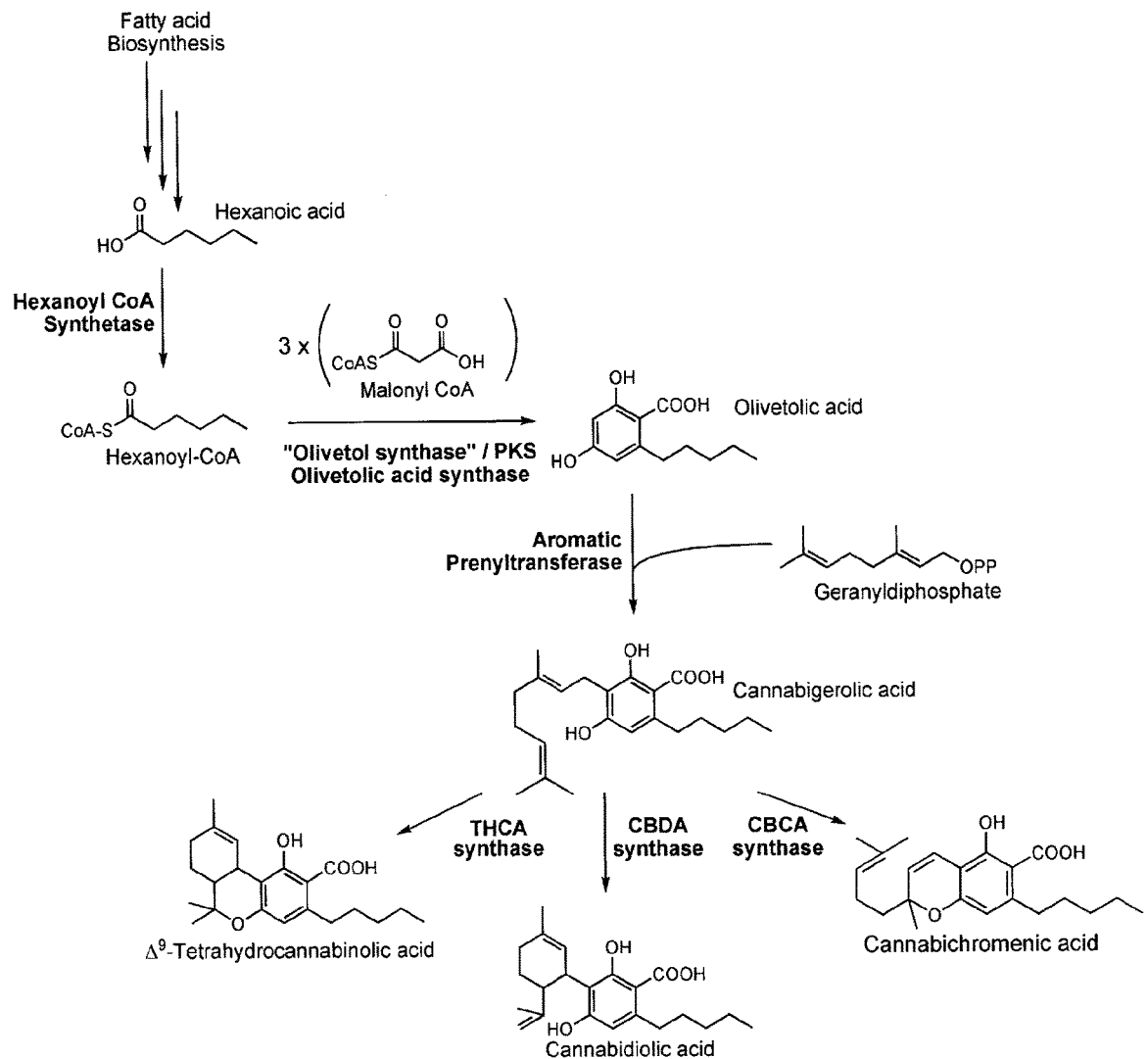
FIG. 1 depicts a proposed pathway leading to the main cannabinoid types in *Cannabis sativa*. Abbreviations: THCA synthase is $\Delta^9$-tetrahydrocannabinolic acid synthase; CBDA synthase is cannabidiolic acid synthase; CBCA synthase is cannabichromenic acid synthase.
Figure 2A:
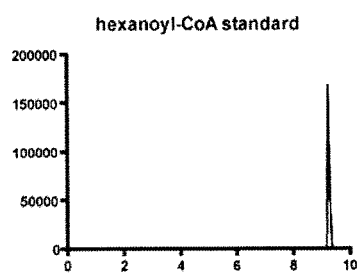
FIGS. 2A-2F depict liquid chromatography-mass spectrometry/mass spectrometry (LC-MS/MS) analysis of the enzymatic activity of *Cannabis sativa* hexanoyl-CoA synthases. Each of FIGS. 2A-2F show ion abundance (m/z 866>359) on the vertical axis and time (minutes) on the horizontal axis.
Figure 2B:
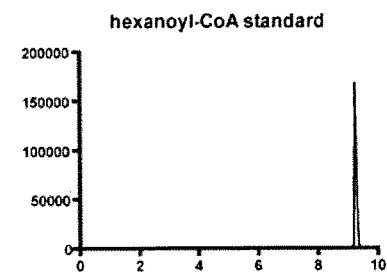
Figure 2C:
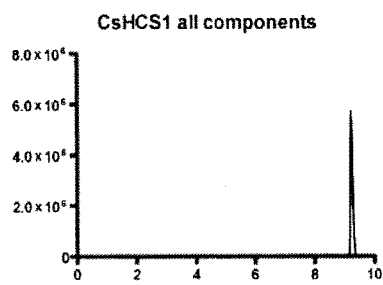
Figure 2D:
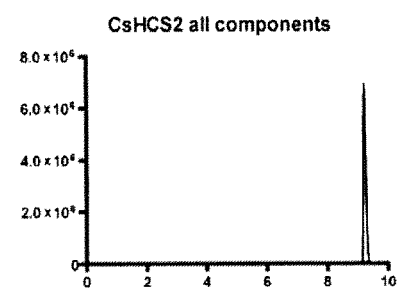
Figure 2E:
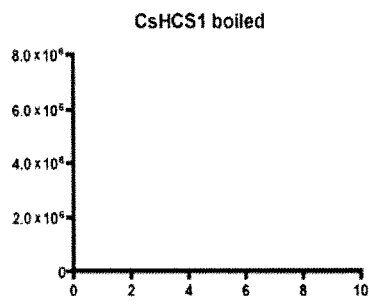
Figure 2F:
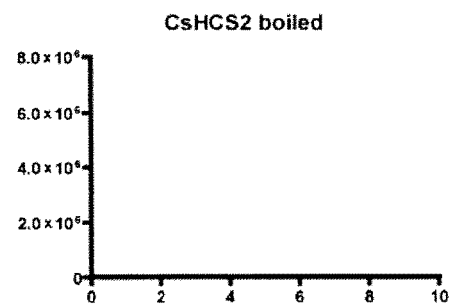

A trichome-specific cDNA library deom *cannabis* was sequenced to produce 9157 express sequence tags ("ESTs") that assembled into 4113 unique sequences (1227 contigs, 2886 singletons). Unigenes were annotated by comparison to the UniProt™ protein database using the online search and comparison tool called blastx. *Cannabis* acyl-activating enzyme proteins were identified by utilizing *Arabidopsis* acyl-activating enzyme sequences to query the assembled *cannabis* ESTs using the online search and comparison tool called tblastn. Eleven acyl-activating enzymes were identified and named according to their transcript abundance in the cDNA library. CsHCS1 was the most abundant acyl-activating enzyme based on transcript levels (42 ESTs); CsHCS2 had lower abundance (5 ESTs) Based on its high transcript levels in trichomes and the localization of CsHCS1 to the cytoplasm, it is likely that this enzyme is the acyl-activating enzyme involved in supplying hexanoyl-CoA to the cannabinoid pathway. CsHCS2, which is localized to the peroxisome, is probably not involved in cannabinoid formation. However, its kinetic properties make it a useful enzyme for synthesizing hexanoyl-CoA in heterologous hosts or in cell-free systems.

The sequence of the CsHCS1 gene is as follows:

*Cannabis sativa* CsHCS1 - 2163 bp
(SEQ ID NO: 1)
ATGGGTAAGAATTACAAGTCCCTGGACTCTGTTGTGGCCTCTGACTTCAT

AGCCCTAGGTATCACCTCTGAAGTTGCTGAGACACTCCATGGTAGACTGG

CCGAGATCGTGTGTAATTATGGCGCTGCCACTCCCCAAACATGGATCAAT

ATTGCCAACCATATTCTGTCGCCTGACCTCCCCTTCTCCCTGCACCAGAT

GCTCTTCTATGGTTGCTATAAAGACTTTGGACCTGCCCCTCCTGCTTGGA

TACCCGACCCGGAGAAAGTAAAGTCCACCAATCTGGGCGCACTTTTGGAG

AAGCGAGGAAAAGAGTTTTTGGGAGTCAAGTATAAGGATCCCATTTCAAG

CTTTTCTCATTTCCAAGAATTTTCTGTAAGAAACCCTGAGGTGTATTGGA

GAACAGTACTAATGGATGAGATGAAGATAAGTTTTTCAAAGGATCCAGAA

TGTATATTGCGTAGAGATGATATTAATAATCCAGGGGGTAGTGAATGGCT

TCCAGGAGGTTATCTTAACTCAGCAAAGAATTGCTTGAATGTAAATAGTA

ACAAGAAATTGAATGATACAATGATTGTATGGCGTGATGAAGGAAATGAT

GATTTGCCTCTAAACAAATTGACACTTGACCAATTGCGTAAACGTGTTTG

GTTAGTTGGTTATGCACTTGAAGAAATGGGTTTGGAGAAGGGTTGTGCAA

TTGCAATTGATATGCCAATGCATGTGGATGCTGTGGTTATCTATCTAGCT

ATTGTTCTTGCGGGATATGTAGTTGTTTCTATTGCTGATAGTTTTTCTGC

TCCTGAAATATCAACAAGACTTCGACTATCAAAAGCAAAAGCCATTTTTA

CACAGGATCATATTATTCGTGGGAAGAAGCGTATTCCCTTATACAGTAGA

GTTGTGGAAGCCAAGTCTCCCATGGCCATTGTTATTCCTTGTAGTGGCTC

TAATATTGGTGCAGAATTGCGTGATGCGATATTTCTTGGGATTACTTTC

TAGAAAGAGCAAAAGAGTTTAAAAATTGTGAATTTACTGCTAGAGAACAA

CCAGTTGATGCCTATACAAACATCCTCTTCTCATCTGGAACAACAGGGGA

GCCAAAGGCAATTCCATGGACTCAAGCAACTCCTTTAAAAGCAGCTGCAG

ATGGGTGGAGCCATTTGGACATTAGGAAAGGTGATGTCATTGTTTGGCCC

ACTAATCTTGGTTGGATGATGGGTCCTTGGCTGGTCTATGCTTCACTCCT

TAATGGGGCTTCTATTGCCTTGTATAATGGATCACCACTTGTTTCTGGCT

TTGCCAAATTTGTGCAGGATGCTAAAGTAACAATGCTAGGTGTGGTCCCT

AGTATTGTTCGATCATGGAAAAGTACCAATTGTGTTAGTGGCTATGATTG

GTCCACCATCCGTTGCTTTTCCTCTTCTGGTGAAGCATCTAATGTAGATG

AATACCTATGGTTGATGGGAGAGCAAACTACAAGCCTGTTATCGAAATG

TGTGGTGGCACAGAAATTGGTGGTGCATTTTCTGCTGGCTCTTTCTTACA

AGCTCAATCATTATCTTCATTTAGTTCACAATGTATGGGTTGCACTTTAT

ACATACTTGACAAGAATGGTTATCCAATGCCTAAAAACAAACCAGGAATT

GGTGAATTAGCGCTTGGTCCAGTCATGTTTGGAGCATCGAAGACTCTGTT

GAATGGTAATCACCATGATGTTTATTTTAAGGGAATGCCTACATTGAATG

GAGAGGTTTTAAGGAGGCATGGGGACATTTTTGAGCTTACATCTAATGGT

TATTATCATGCACATGGTCGTGCAGATGATACAATGAATATTGGAGGCAT

CAAGATTAGTTCCATAGAGATTGAACGAGTTTGTAATGAAGTTGATGACA

GAGTTTTCGAGACAACTGCTATTGGAGTGCCACCTTTGGGCGGTGGACCT

GAGCAATTAGTAATTTTCTTTGTATTAAAAGATTCAAATGATACAACTAT

TGACTTAAATCAATTGAGGTTATCTTTCAACTTGGGTTTACAGAAGAAAC

TAAATCCTCTGTTCAAGGTCACTCGTGTTGTGCCTCTTTCATCACTTCCG

AGAACAGCAACCAACAAGATCATGAGAAGGGTTTTGCGCCAGCAATTTTC

TCACTTTGAATGA

The sequence of the CsHCS2 gene is as follows:

*Cannabis sativa* CsHCS2 - 1547 bp
(SEQ ID NO: 3)
ATGGAGAAATCTTTTTCAGAAACTCATCTTCATACCCACAAAAGCCAGCT

CTCATTGATTCCGAAACCAACCAAATACTCTCCTTTTCCCACTTCAAATC

TACGGTTATCAAGGTCTCCCATGGCTTTCTCAATCTGGGTATCAAGAAAA

ACGACGTCGTTCTCATCTACGCCCCTAATTCTATCCACTTCCCTGTTTGT

TTCCTGGGAATTATAGCCTCTGGAGCCATTGCCACTACCTCAAATCCTCT

CTACACAGTTTCCGAGCTTTCCAAACAGGTCAAGGATTCCAATCCCAAAC

TCATTATCACCGTTCCTCAACTCTTGGAAAAAGTAAAGGGTTTCAATCTC

CCCACGATTCTAATTGGTCCTGATTCTGAACAAGAATCTTCTAGTGATAA

AGTAATGACCTTTAACGATTTGGTCAACTTAGGTGGGTCGTCTGGCTCAG

AATTTCCAATTGTTGATGATTTTAAGCAGAGTGACACTGCTGCGCTATTG

TACTCATCTGGCACAACGGGAATGAGTAAAGGTGTGGTTTTGACTCACAA

AAACTTCATTGCCTCTTCTTTAATGGTGACAATGGAGCAAGACCTAGTTG

GAGAGATGGATAATGTGTTTCTATGCTTTTTGCCAATGTTTCATGTATTT

GGTTTGGCTATCATCACCTATGCTCAGTTGCAGAGAGGAAACACTGTTAT

-continued

```
TTCAATGGCGAGATTTGACCTTGAGAAGATGTTAAAAGATGTGGAAAAGT

ATAAAGTTACCCATTTGTGGGTTGTGCCTCCTGTGATACTGGCTCTGAGT

AAGAACAGTATGGTGAAGAAGTTTAATCTTTCTTCTATAAAGTATATTGG

CTCCGGTGCAGCTCCTTTGGGCAAAGATTTAATGGAGGAGTGCTCTAAGG

TTGTTCCTTATGGTATTGTTGCTCAGGGATATGGTATGACAGAAACTTGT

GGGATTGTATCCATGGAGGATATAAGAGGAGGTAAACGAAATAGTGGTTC

AGCTGGAATGCTGGCATCTGGAGTAGAAGCCCAGATAGTTAGTGTAGATA

CACTGAAGCCCTTACCTCCTAATCAATTGGGGGAGATATGGGTGAAGGGG

CCTAATATGATGCAAGGTTACTTCAATAACCCACAGGCAACCAAGTTGAC

TATAGATAAGAAAGGTTGGGTACATACTGGTGATCTTGGATATTTTGATG

AAGATGGACATCTTTATGTTGTTGACCGTATAAAAGAGCTCATCAAATAT

AAAGGATTTCAGGTTGCTCCTGCTGAGCTTGAAGGATTGCTTGTTTCTCA

CCCTGAAATACTCGATGCTGTTGTGATTCCATTTCCTGACGCTGAAGCGG

GTGAAGTCCCAGTTGCTTATGTTGTGCGCTCTCCCAACAGTTCATTAACC

GAAAATGATGTGAAGAAATTTATCGCGGGCCAGGTTGCATCTTTCAAAAG

ATTGAGAAAAGTAACATTTATAAACAGTGTCCCGAAATCTGCTTCGGGGA

AAATCCTCAGAAGAGAACTCATTCAGAAAGTACGCTCCAACATGTGA
```

CsHCS1 and CsHCS2 were PCR amplified as described in Example 1 and the alkanoyl-CoA synthetase or CoA-ligase activity was measured as described in Example 2. As is shown in FIG. 2, CsHCS1 and CsHCS2 catalyze the production of alkanoyl-CoA from a carboxylic acid and CoA.

Some embodiments of the present invention relate to an isolated or purified nucleic acid molecule having SEQ ID NO: 1 or having at least 75%, at least 76%, least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to SEQ ID NO: 1.

Some embodiments of the present invention relate to an isolated or purified nucleic acid molecule having SEQ ID NO: 3 or having at least 75%, at least 76%, least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to SEQ ID NO: 3.

Further included are nucleic acid molecules that hybridize to the above disclosed nucleic acid sequences. Hybridization conditions may be stringent in that hybridization will occur if there is at least a 90%, 95% or 97% sequence identity with the nucleic acid molecule that encodes the enzyme of the present invention. The stringent conditions may include those used for known Southern hybridizations such as, for example, incubation overnight at 42° C. in a solution having 50% formamide, 5×SSC (150 mM NaCl, 15 mM trisodium citrate), 50 mM sodium phosphate (pH 7.6), 5×Denhardt's solution, 10% dextran sulfate, and 20 micrograms/milliliter denatured, sheared salmon sperm DNA, following by washing the hybridization support in 0.1×SSC at about 65° C. Other known hybridization conditions are well known and are described in Sambrook et al., Molecular Cloning: A Laboratory Manual, Third Edition, Cold Spring Harbor, N.Y. (2001).

As will be appreciated by the skilled practitioner, slight changes in nucleic acid sequence do not necessarily alter the amino acid sequence of the encoded polypeptide. It will be appreciated by persons skilled in the art that changes in the identities of nucleotides in a specific gene sequence that change the amino acid sequence of the encoded polypeptide may result in reduced or enhanced effectiveness of the genes and that, in some applications (e.g. anti-sense, co suppression, or RNAi), partial sequences often work as effectively as full length versions. The ways in which the nucleotide sequence can be varied or shortened are well known to persons skilled in the art, as are ways of testing the effectiveness of the altered genes. In certain embodiments, effectiveness may easily be tested by, for example, conventional gas chromatography. All such variations of the genes are therefore included as part of the present disclosure.

As will be appreciated by one of skill in the art, the length of the nucleic acid molecule described above will depend on the intended use. For example, if the intended use is as a primer or probe, for example for PCR amplification or for screening a library, the length of the nucleic acid molecule will be less than the full length sequence, for example, 15-50 nucleotides. In these embodiments, the primers or probes may be substantially identical to a highly conserved region of the nucleic acid sequence or may be substantially identical to either the 5' or 3' end of the DNA sequence. In some cases, these primers or probes may use universal bases in some positions so as to be 'substantially identical' but still provide flexibility in sequence recognition. It is of note that suitable primer and probe hybridization conditions are well known in the art.

The present invention also includes the enzyme CsHCS1. The amino acid sequence of CsHCS1 (SEQ ID NO: 2) is:

```
MGKNYKSLDSVVASDFIALGITSEVAETLHGRLAEIVCNYGAATPQTWIN

IANHILSPDLPFSLHQMLFYGCYKDFGPAPPAWIPDPEKVKSTNLGALLE

KRGKEFLGVKYKDPISSFSHFQEFSVRNPEVYWRTVLMDEMKISFSKDPE

CILRRDDINNPGGSEWLPGGYLNSAKNCLNVNSNKKLNDTMIVWRDEGND

DLPLNKLTLDQLRKRVWLVGYALEEMGLEKGCAIAIDMPMHVDAVVIYLA

IVLAGYVVVSIADSFSAPEISTRLRLSKAKAIFTQDHIIRGKKRIPLYSR

VVEAKSPMAIVIPCSGSNIGAELRDGDISWDYFLERAKEFKNCEFTAREQ

PVDAYTNILFSSGTTGEPKAIPWTQATPLKAAADGWSHLDIRKGDVIVWP

TNLGWMMGPWLVYASLLNGASIALYNGSPLVSGFAKFVQDAKVTMLGVVP

SIVRSWKSTNCVSGYDWSTIRCFSSSGEASNVDEYLWLMGRANYKPVIEM

CGGTEIGGAFSAGSFLQAQSLSSFSSQCMGCTLYILDKNGYPMPKNKPGI

GELALGPVMFGASKTLLNGNHHDVYFKGMPTLNGEVLRRHGDIFELTSNG

YYHAHGRADDTMNIGGIKISSIEIERVCNEVDDRVFETTAIGVPPLGGGP

EQLVIFFVLKDSNDTTIDLNQLRLSFNLGLQKKLNPLFKVTRVVPLSSLP

RTATNKIMRRVLRQFSHFE
```

Some embodiments relate to an isolated or purified polypeptide having SEQ ID NO. 2 or having at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence as set forth in SEQ ID NO: 2.

The present invention also includes the enzyme CsHCS2. The amino acid sequence of CsHCS2 (SEQ ID NO: 4) is:

MEKSGYGRDGIYRSLRPPLHLPNNNNLSMVSFLFRNSSSYPQKPALIDSE

TNQILSFSHFKSTVIKVSHGFLNLGIKKNDVVLIYAPNSIHFPVCFLGII

ASGAIATTSNPLYTVSELSKQVKDSNPKLIITVPQLLEKVKGFNLPTILI

GPDSEQESSSDKVMTFNDLVNLGGSSGSEFPIVDDFKQSDTAALLYSSGT

TGMSKGVVLTHKNFIASSLMVTMEQDLVGEMDNVFLCFLPMFHVFGLAII

TYAQLQRGNTVISMARFDLEKMLKDVEKYKVTHLWVVPPVILALSKNSMV

KKFNLSSIKYIGSGAAPLGKDLMEECSKVVPYGIVAQGYGMTETCGIVSM

EDIRGGKRNSGSAGMLASGVEAQIVSVDTLKPLPPNQLGEIWVKGPNMMQ

GYFNNPQATKLTIDKKGWVHTGDLGYFDEDGHLYVVDRIKELIKYKGFQV

APAELEGLLVSHPEILDAVVIPFPDAEAGEVPVAYVVRSPNSSLTENDVK

KFIAGQVASFKRLRKVTFINSVPKSASGKILRRELIQKVRSNM

Some embodiments relate to an isolated or purified polypeptide having SEQ ID NO. 4 or having at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence as set forth in SEQ ID NO: 4.

Some embodiments relate to a vector, construct or expression system containing an isolated or purified polynucleotide having the sequence of SEQ ID NO: 1 or SEQ ID NO: 3, or least 75%, at least 76%, least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to SEQ ID NO: 1 or SEQ ID NO: 3. As well, there is provided a method for preparing a vector, construct or expression system including such a sequence, or a part thereof, for introduction of the sequence or partial sequence in a sense or anti-sense orientation, or a complement thereof, into a cell.

In some embodiments, the isolated and/or purified nucleic acid molecules, or vectors, constructs or expression systems comprising these isolated and/or purified nucleic acid molecules, may be used to create transgenic organisms or cells of organisms that produce polypeptides which catalyze the synthesis of aromatic polyketides. Therefore, one embodiment relates to transgenic organisms, cells or germ tissues of the organism comprising an isolated and/or purified nucleic acid molecule having SEQ ID NO: 1 or SEQ ID NO: 3 or having least 75%, at least 76%, least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to SEQ ID NO: 1 or SEQ ID NO: 3.

Preferably, the organism is a plant, microorganism or insect. Plants are preferably of the genus *Cannabis*, for example *Cannabis sativa* L., *Cannabis indica* Lam. and *Cannabis ruderalis* Janisch. Especially preferred is *Cannabis sativa*. Microorganisms are preferably bacteria (e.g. *Escherichia coli*) or yeast (e.g. *Saccharomyces cerevisiae*). Insect is preferably *Spodoptera frugiperda*.

Organisms, cells and germ tissues of this embodiment may have altered levels of cannabinoid compounds. With reference to FIG. 1, it will be appreciated by one skilled in the art that expression or over-expression of the nucleic acid molecules of the invention will result in expression or over-expression of the enzyme that catalyzes the synthesis of hexanoyl-CoA which, in combination with other enzymes, may result in the production or increased production of cannabinoid compounds such as cannabigerolic acid (CBGA), $\Delta^9$-tetrahydrocannabinolic acid (THCA), cannabidiolic acid (CBDA), cannabichromenic acid (CBCA), $\Delta^9$-tetrahydrocannabinol (THC), cannabidiol (CBD), cannabichromene (CBC), etc. Similarly, depending on the substrate used, expression or over-expression of the nucleic acid molecules of the invention resulting in expression or over-expression of the enzyme that catalyzes the synthesis of hexanoyl-CoA may result in the production or increased production of analogs of cannabinoid compounds, or analogs of precursors of such compounds.

Silencing of the gene in the organism, cell or tissue will result in under-expression of the enzyme which may result in accumulation of precursors such as hexanoic acid (six carbons), octanoic acid (eight carbons), nonanoic acid (nine carbons), valeric acid (five carbons), heptanoic acid (seven carbons) or other carboxylic acids, and/or reduction of cannabinoids such as THCA (the precursor of THC) or CBDA (the precursor of CBD).

The present invention includes a process of altering levels of cannabinoid compounds in an organism, cell or tissue by expressing or over-expressing an exogenous enzyme of the invention in the organism, cell or tissue, in comparison to a similar variety of organism, cell or tissue grown under similar conditions but without an exogenous enzyme of the invention being expressed or over-expressed.

Expression or over-expression of the nucleic acid molecules of the invention may be done in combination with expression or over-expression of one or more other nucleic acids that encode one or more enzymes in a cannabinoid biosynthetic pathway. Some examples of other nucleic acids include those which encode: a type III polyketide synthase, a polyketide cyclase, an aromatic prenyltransferase and a cannabinoid-forming oxidocylase. Specific examples of these enzymes include "olivetol synthase"/polyketide synthase, olivetolic acid synthase, a geranylpyrophosphate: olivetolate geranyltransferase, a $\Delta^9$-tetrahydrocannabinolic acid synthase, a cannabidiolic acid synthase or a cannabichromenic acid synthase. Synthesis of alkanoyl-CoA in the presence of an enzyme polypeptide of the present invention may be accomplished in vivo or in vitro. As previously mentioned, such syntheses in vivo may be accomplished by expressing or over-expressing the nucleic acid molecule of the invention in an organism, cell or tissue.

Synthesis of alkanoyl-CoA in vitro can take place in a cell-free system. As part of an in vitro cell-free system, the carboxylic acid and an enzyme of the present invention may be mixed together in a suitable reaction vessel to effect the reaction.

In vitro, the polypeptides of the present invention may be used in combination with other enzymes to effect a complete synthesis of a cannabinoid compound from a precursor. For example, such other enzymes may be implicated in a cannabinoid biosynthetic pathway as described in FIG. 1 (such as "olivetol synthase"/PKS, olivetolic acid synthase, aromatic prenyltransferase, THCA synthase, CBDA synthase, CBCA synthase).

The polypeptides of the present invention may be used, in vivo or in vitro, to synthesize analogs of cannabinoid compounds which are not naturally occurring in the host species. Such analogs can be produced using carboxylic acid compounds other than those used to produce natural cannabinoid compounds in plants. For example, acetic acid, butyric acid, octanoic acid, decanoic acid, lauric acid, myristic acid, palmitic acid; branched chain acids such isovaleric acid; and hydroxycinnamic acids such a cinnamic acid.

TERMS

In order to facilitate review of the various embodiments of the disclosure, the following explanations of specific terms are provided:

Alkanoyl-CoA: An alkanoyl-CoA is an aliphatic carbonyl compound having a coenzyme A moiety bonded to the carbon atom of the carbonyl group through a sulfide bridge. Preferred alkanoyl-CoA compounds comprise from 2 to 10 carbon atoms in the aliphatic carbonyl part of the compound. More preferably, the alkanoyl-CoA is CoA-S—C(O)—$(CH_2)_n$—$CH_3$, where n is an integer from 0 to 8. Some examples of alkanoyl-CoA compounds are acetyl-CoA, butyryl-CoA, hexanoyl-CoA and octanoyl-CoA. Use of acetyl-CoA provides a methyl side chain to the resulting aromatic polyketide; use of butyryl-CoA provides a propyl side chain; and use of hexanoyl-CoA provides a pentyl side chain. Hexanoyl-CoA is especially preferred. Cannabinoids with shorter side-chains exist in *cannabis* (e.g. tetrahydrocannabivarinic acid having a propyl side-chain instead of the pentyl side-chain of THCA).

Codon degeneracy: It will be appreciated that this disclosure embraces the degeneracy of codon usage as would be understood by one of ordinary skill in the art and as illustrated in Table 1.

TABLE 1

Codon Degeneracies

| Amino Acid | Codons |
| --- | --- |
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, UGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |
| START | ATG |
| STOP | TAG, TGA, TAA |

Complementary nucleotide sequence: "Complementary nucleotide sequence" of a sequence is understood as meaning any nucleic acid molecule whose nucleotides are complementary to those of a sequence disclosed herein, and whose orientation is reversed (anti-parallel sequence).

Conservative substitutions: It will be understood by one skilled in the art that conservative substitutions may be made in the amino acid sequence of a polypeptide without disrupting the three-dimensional structure or function of the polypeptide. Accordingly, the present invention includes polypeptides comprising conservatively substituted CsHCS1 and CsHCS2. Conservative substitutions are accomplished by the skilled artisan by substituting amino acids with similar hydrophobicity, polarity, and R-chain length for one another. Additionally, by comparing aligned sequences of homologous proteins from different species, conservative substitutions may be identified by locating amino acid residues that have been mutated between species without altering the basic functions of the encoded proteins. Table 2 provides an exemplary list of conservative substitutions.

TABLE 2

Conservative Substitutions

| Type of Amino Acid | Substitutable Amino Acids |
| --- | --- |
| Hydrophilic | Ala, Pro, Gly, Glu, Asp, Gln, Asn, Ser, Thr |
| Sulphydryl | Cys |
| Aliphatic | Val, Ile, Leu, Met |
| Basic | Lys, Arg, His |
| Aromatic | Phe, Tyr, Trp |

Degree or percentage of sequence homology: The term "degree or percentage of sequence homology" refers to degree or percentage of sequence identity between two sequences after optimal alignment.

Homologous isolated and/or purified sequence: "Homologous isolated and/or purified sequence" is understood to mean an isolated and/or purified sequence having a percentage identity with the bases of a nucleotide sequence, or the amino acids of a polypeptide sequence, of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7%. This percentage is purely statistical, and it is possible to distribute the differences between the two nucleotide or amino acid sequences at random and over the whole of their length. Sequence identity can be determined, for example, by computer programs designed to perform single and multiple sequence alignments.

Increasing, decreasing, modulating, altering or the like: As will be appreciated by one of skill in the art, such terms refer to comparison to a similar variety or strain grown under similar conditions but without the modification resulting in the increase, decrease, modulation or alteration. In some cases, this may be an untransformed control, a mock transformed control, or a vector-transformed control.

Isolated: As will be appreciated by one of skill in the art, "isolated" refers to polypeptides or nucleic acids that have been "isolated" from their native environment.

Nucleotide, polynucleotide, or nucleic acid sequence: "Nucleotide, polynucleotide, or nucleic acid sequence" will be understood as meaning both double-stranded or single-stranded in the monomeric and dimeric (so-called in tandem) forms and the transcription products thereof.

Sequence identity: Two amino acid or nucleotide sequences are said to be "identical" if the sequence of amino acids or nucleotides in the two sequences is the same when aligned for maximum correspondence as described below. Percentage of sequence identity (or degree of identity) is determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino acid residue or nucleic acid base occurs in both sequences to yield the number of matched positions, dividing the number of matched positions by the total number of positions in the window of comparison and multiplying the result by 100 to yield the percentage of sequence identity.

Optimal alignment of sequences for comparison may be conducted by the local homology algorithm of Smith and Waterman, Ad. App. Math 2: 482 (1981), by the homology alignment algorithm of Needleman and Wunsch, J. Mol. Biol. 48: 443 (1970), by the search for similarity method of Pearson and Lipman, Proc. Natl. Acad. Sci. (U.S.A.) 85: 2444 (1988), by computerized implementation of these algorithms (GAP, BESTFIT, FASTA, and TFASTA in the Wisconsin Genetics Software Package, Genetics Computer Group (GCG), 575 Science Dr., Madison, Wis.), or by visual inspection.

The definition of sequence identity given above is the definition that would be used by one of skill in the art. The definition by itself does not need the help of any algorithm, said algorithms being helpful only to achieve the optimal alignments of sequences, rather than the calculation of sequence identity.

From the definition given above, it follows that there is a well defined and only one value for the sequence identity between two compared sequences which value corresponds to the value obtained for the best or optimal alignment.

Stringent hybridization: Hybridization under conditions of stringency with a nucleotide sequence is understood as meaning a hybridization under conditions of temperature and ionic strength chosen in such a way that they allow the maintenance of the hybridization between two fragments of complementary nucleic acid molecules.

Homologs of the novel genes described herein obtained from other organisms, for example plants, may be obtained by screening appropriate libraries that include the homologs, wherein the screening is performed with the nucleotide sequence of the specific genes of the invention, or portions or probes thereof, or identified by sequence homology search using sequence alignment search programs such as BLAST or FASTA.

Nucleic acid isolation and cloning is well established. Similarly, an isolated gene may be inserted into a vector and transformed into a cell by conventional techniques which are known to those of skill in the art. Nucleic acid molecules may be transformed into an organism. As known in the art, there are a number of ways by which genes, vectors, constructs and expression systems can be introduced into organisms, and a combination of transformation and tissue culture techniques have been successfully integrated into effective strategies for creating transgenic organisms. These methods, which can be used in the invention, have been described elsewhere (Potrykus I (1991) Gene transfer to plants: Assessment of published approaches and results. *Annu. Rev. Plant Physiol. Plant Mol. Biol.* 42: 205-225; Vasil I K (1994) Molecular improvement of cereals. *Plant Mol. Biol.* 25: 925-937. Walden R, Wingender R (1995) Gene-transfer and plant regeneration techniques. *Trends in Biotechnology* 13: 324-331; Songstad D D, Somers D A, Griesbach R J (1995) Advances in alternative DNA delivery techniques. *Plant Cell Tissue Organ Cult.* 40:1-15), and are well known to persons skilled in the art.

Suitable vectors are well known to those skilled in the art and are described in general technical references such as Pouwels et al., *Cloning Vectors. A Laboratory Manual*, Elsevier, Amsterdam (1986). Particularly suitable vectors include the Ti plasmid vectors. For example, one skilled in the art will certainly be aware that, in addition to *Agrobacterium* mediated transformation of *Arabidopsis* by vacuum infiltration (Bechtold N, Ellis J, Pelletier G (1993) In planta *Agrobacterium*-mediated gene transfer by infiltration of adult *Arabidopsis thaliana* plants. *C R Acad Sci Paris, Sciences de la vie/Life sciences* 316: 1194-1199.) or wound inoculation (Katavic V, Haughn G W, Reed D, Martin M, Kunst L (1994) In planta transformation of *Arabidopsis thaliana*. *Mol. Gen. Genet.* 245: 363-370.), it is equally possible to transform other plant species, using *Agrobacterium* Ti-plasmid mediated transformation (e.g., hypocotyl (DeBlock M, DeBrouwer D, Tenning P (1989) Transformation of *Brassica napus* and *Brassica oleracea* using *Agrobacterium tumefaciens* and the expression of the bar and neo genes in the transgenic plants. *Plant Physiol.* 91: 694-701) or cotyledonary petiole (Moloney M M, Walker J M, Sharma K K (1989) High efficiency transformation of *Brassica napus* using *Agrobacterium* vectors. *Plant Cell Rep.* 8: 238-242.) wound infection, particle bombardment/biolistic methods (Sanford J C, Klein T M, Wolf E D, Allen N (1987) Delivery of substances into cells and tissues using a particle bombardment process. *J. Part. Sci. Technol.* 5: 27-37.) or polyethylene glycol-assisted, protoplast transformation methods (Rhodes C A, Pierce D A, Mettler I J, Mascarenhas D, Detmer J J (1988) Genetically transformed maize plants from protoplasts. *Science* 240: 204-207).

As will also be apparent to persons skilled in the art, and as described elsewhere (Meyer P (1995) Understanding and controlling transgene expression. *Trends in Biotechnology* 13: 332-337; Datla R, Anderson J W, Selvaraj G (1997) Plant promoters for transgene expression. Biotechnology Annual Review 3: 269-296.), it is possible to utilize promoters operatively linked to the nucleic acid molecule to direct any intended up- or down-regulation of transgene expression using unregulated (i.e. constitutive) promoters (e.g., those based on CaMV35S), or by using promoters which can target gene expression to particular cells, tissues (e.g., napin promoter for expression of transgenes in developing seed cotyledons), organs (e.g., roots), to a particular developmental stage, or in response to a particular external stimulus (e.g., heat shock).

Promoters for use in the invention may be inducible, constitutive, or tissue-specific or have various combinations of such characteristics. Useful promoters include, but are not limited to constitutive promoters such as carnation etched ring virus promoter (CERV), cauliflower mosaic virus (CaMV) 35S promoter, or more particularly the double enhanced cauliflower mosaic virus promoter, comprising two CaMV 35S promoters in tandem (referred to as a "Double 35S" promoter). It may be desirable to use a tissue-specific or developmentally regulated promoter instead of a constitutive promoter in certain circumstances. A tissue-specific promoter allows for over-expression in certain tissues without affecting expression in other tissues.

The promoter and termination regulatory regions will be functional in the host cell and may be heterologous (that is, not naturally occurring) or homologous (derived from the host species) to the cell and the gene.

The termination regulatory region may be derived from the 3' region of the gene from which the promoter was obtained or from another gene. Suitable termination regions which may be used are well known in the art and include

*Agrobacterium tumefaciens* nopaline synthase terminator (Tnos), *A. tumefaciens* mannopine synthase terminator (Tmas) and the CaMV 35S terminator (T35S). Particularly preferred termination regions for use in the present invention include the pea ribulose bisphosphate carboxylase small subunit termination region (TrbcS) or the Tnos termination region. Gene constructs for use in the invention may suitably be screened for activity by, for example, transformation into a host plant via *Agrobacterium* and screening for altered cannabinoid levels.

The nucleic acid molecules of the invention, or fragments thereof, may be used to block cannabinoid biosynthesis in organisms that naturally produce cannabinoid compounds. Silencing using a nucleic acid molecule of the invention may be accomplished in a number of ways generally known in the art, for example, RNA interference (RNAi) techniques, artificial microRNA techniques, virus-induced gene silencing (VIGS) techniques, antisense techniques, sense co-suppression techniques and targeted mutagenesis techniques.

RNAi techniques involve stable transformation using RNA interference (RNAi) plasmid constructs (Helliwell C A, Waterhouse P M (2005) Constructs and methods for hairpin RNA-mediated gene silencing in plants. *Methods Enzymology* 392:24-35). Such plasmids are composed of a fragment of the target gene to be silenced in an inverted repeat structure. The inverted repeats are separated by a spacer, often an intron. The RNAi construct driven by a suitable promoter, for example, the Cauliflower mosaic virus (CaMV) 35S promoter, is integrated into the plant genome and subsequent transcription of the transgene leads to an RNA molecule that folds back on itself to form a double-stranded hairpin RNA. This double-stranded RNA structure is recognized by the plant and cut into small RNAs (about 21 nucleotides long) called small interfering RNAs (siRNAs). The siRNAs associate with a protein complex (RISC) which goes on to direct degradation of the mRNA for the target gene.

Artificial microRNA (amiRNA) techniques exploit the microRNA (miRNA) pathway that functions to silence endogenous genes in plants and other eukaryotes (Schwab R, Ossowski S, Riester M, Warthmann N, Weigel D (2006) Highly specific gene silencing by artificial microRNAs in *Arabidopsis*. *Plant Cell* 18:1121-33; Alvarez J P, Pekker I, Goldshmidt A, Blum E, Amsellem Z, Eshed Y (2006) Endogenous and synthetic microRNAs stimulate simultaneous, efficient, and localized regulation of multiple targets in diverse species. *Plant Cell* 18:1134-51). In this method, 21 nucleotide long fragments of the gene to be silenced are introduced into a pre-miRNA gene to form a pre-amiRNA construct. The pre-amiRNA construct is transferred into the organism genome using transformation methods which would be apparent to one skilled in the art. After transcription of the pre-amiRNA, processing yields amiRNAs that target genes which share nucleotide identity with the 21 nucleotide amiRNA sequence.

In RNAi silencing techniques, two factors can influence the choice of length of the fragment. The shorter the fragment the less frequently effective silencing will be achieved, but very long hairpins increase the chance of recombination in bacterial host strains. The effectiveness of silencing also appears to be gene dependent and could reflect accessibility of target mRNA or the relative abundances of the target mRNA and the hairpin RNA in cells in which the gene is active. A fragment length of between 100 and 800 bp, preferably between 300 and 600 bp, is generally suitable to maximize the efficiency of silencing obtained. The other consideration is the part of the gene to be targeted. 5' UTR, coding region, and 3' UTR fragments can be used with equally good results. As the mechanism of silencing depends on sequence homology, there is potential for cross-silencing of related mRNA sequences. Where this is not desirable, a region with low sequence similarity to other sequences, such as a 5' or 3' UTR, should be chosen. The rule for avoiding cross-homology silencing appears to be to use sequences that do not have blocks of sequence identity of over 20 bases between the construct and the non-target gene sequences. Many of these same principles apply to selection of target regions for designing amiRNAs.

Virus-induced gene silencing (VIGS) techniques are a variation of RNAi techniques that exploits the endogenous antiviral defenses of plants. Infection of plants with recombinant VIGS viruses containing fragments of host DNA leads to post-transcriptional gene silencing for the target gene. In one embodiment, a tobacco rattle virus (TRV) based VIGS system can be used with the nucleotide sequences of the present invention.

Antisense techniques involve introducing into a plant an antisense oligonucleotide that will bind to the messenger RNA (mRNA) produced by the gene of interest. The "antisense" oligonucleotide has a base sequence complementary to the gene's messenger RNA (mRNA), which is called the "sense" sequence. Activity of the sense segment of the mRNA is blocked by the anti-sense mRNA segment, thereby effectively inactivating gene expression. Application of antisense to gene silencing in plants is described in more detail by Stam M, de Bruin R, van Blokland R, van der Hoorn R A, Mol J N, Kooter J M (2000) Distinct features of post-transcriptional gene silencing by antisense transgenes in single copy and inverted T-DNA repeat loci. *Plant J.* 21:27-42.

Sense co-suppression techniques involve introducing a highly expressed sense transgene into a plant resulting in reduced expression of both the transgene and the endogenous gene (Depicker A, Montagu M V (1997) Post-transcriptional gene silencing in plants. *Curr Opin Cell Biol.* 9: 373-82). The effect depends on sequence identity between transgene and endogenous gene.

Targeted mutagenesis techniques, for example TILLING (Targeting Induced Local Lesions IN Genomes) and "delete-a-gene" using fast-neutron bombardment, may be used to knockout gene function in an organism (Henikoff S, Till B J, Comai L (2004) TILLING. Traditional mutagenesis meets functional genomics. *Plant Physiol* 135:630-6; Li X, Lassner M, Zhang Y. (2002) Deleteagene: a fast neutron deletion mutagenesis-based gene knockout system for plants. Comp Funct Genomics. 3: 158-60). TILLING involves treating germplasm or individual cells with a mutagen to cause point mutations that are then discovered in genes of interest using a sensitive method for single-nucleotide mutation detection. Detection of desired mutations (e.g. mutations resulting in the inactivation of the gene product of interest) may be accomplished, for example, by PCR methods. For example, oligonucleotide primers derived from the gene of interest may be prepared and PCR may be used to amplify regions of the gene of interest from organisms in the mutagenized population. Amplified mutant genes may be annealed to wild-type genes to find mismatches between the mutant genes and wild-type genes. Detected differences may be traced back to the organism which had the mutant gene thereby revealing which mutagenized organism will have the desired expression (e.g. silencing of the gene of interest). These organisms may then be selectively bred to produce a population having the desired expression. TILLING can provide an allelic series that includes missense and knockout mutations, which exhibit reduced expression of the targeted gene. TILLING is touted as a possible approach to gene knockout that does not involve introduction of transgenes, and therefore may be more acceptable to consumers. Fast-neutron bombardment induces mutations, i.e. deletions, in organism genomes that can also be detected using PCR in a manner similar to TILLING.

It will be understood by one of skill in the art that the processes of the invention can also be carried out in a cell-free environment in the presence of one or more carboxylic acids.

Embodiments of the invention are susceptible to various modifications and alternative forms in addition to the specific examples included herein. Thus, embodiments of the invention are not limited to the particular forms disclosed.

EXAMPLES

Example 1

Amplification and Cloning of CsHCS1 and CsHCS2

CsHCS1 and CsHCS2 were PCR amplified from cDNA plasmid clones using the primers listed in Table 3 and Phusion™ polymerase (Finnzymes). PCR products were purified and cloned into the pCR8/GW/TOPO entry vector (Invitrogen). After transformation into E. coli TOP10 cells (Invitrogen), individual clones were verified by sequencing. The CsHCS1 and CsHCS2 genes were recombined into the pHIS8/GW destination vector using LR recombinase (Invitrogen). The LR reaction products were transformed into TOP10 cells and verified by sequencing.

TABLE 3

| Oligonucleotides | |
|---|---|
| Name | Sequence (5'-3') |
| CsHCS1 forward (SEQ ID NO: 5) | ATGGGTAAGAATTACAAGTCCCT |
| CsHCS1 reverse (SEQ ID NO: 6) | GAGCTCTCATTCAAAGTGAGAAAATTGCTG |
| CsHCS2 forward (SEQ ID NO: 7) | ATGGAGAAATCTGGGTATGGAAG |
| CsHCS2 reverse (SEQ ID NO: 8) | TCACATGTTGGAGCGTACTTTC |
| MCS forward (SEQ ID NO: 9) | ATGAGCAACCATCTTTTCGACG |
| MCS reverse (SEQ ID NO: 10) | TTACGTCCTGGTATAAAGATCGGC | pHIS8/GW-CsHCS1 and pHIS8/GW-CsHCS2 were transformed into E. coli Rosetta 2 cells (Merck). Individual colonies were used to inoculate small-scale cultures of liquid LB medium containing chloramphenicol and kanamycin, which were used to inoculate 500 mL of liquid LB medium without antibiotics. After growth to $OD_{600}$ of 0.6, expression was induced by the addition of IPTG to 0.2 µM. The CsHCS1 expressing cultures were then grown at 12° C. with shaking for 24 h, whereas the CsHCS2 cultures were grown at 37° C. for 16 h. Different temperatures were used because it was observed that CsHCS1 did not produce soluble protein at the higher temperature.

Cells were harvested by centrifugation and resuspended in 10 mL His-tag lysis buffer (50 mM Tris-HCl pH 7, 500 mM NaCl, 2.5 mM imidazole, 10% v/v glycerol, 10 mM β-mercaptoethanol, 1% v/v Tween™ 20, and 750 µg/mL lysozyme). The resuspended cells were incubated on ice for 1 h then lysed by sonication. After centrifugation for 20 min at 12,000 g at 4° C., the soluble protein fraction was added to 160 µL of Talon™ resin (Clontech) that had previously been washed with His-tag wash buffer (HWB; 50 mM Tris-HCl pH 7, 500 mM NaCl, 2.5 mM imidazole, 10% glycerol, 10 mM β-mercaptoethanol). The samples were incubated with gentle rocking at 4° C., after which the resin was isolated by centrifugation (700 g for 5 min). The resin was resuspended in HWB buffer and washed with gentle rocking at 4° C. then centrifuged. The wash step was then repeated twice and the resuspended resin loaded onto a chromatography column and allowed to drain. After washing the resin with 10 mL of HWB buffer, the His-tagged proteins were eluted by the addition of 2.5 mL of His-tag elution buffer (50 mM Tris-HCl pH 7, 500 mM NaCl, 250 mM imidazole, 10% v/v glycerol, 10 mM β-mercaptoethanol). The eluates were buffer exchanged into storage buffer (50 mM HEPES pH 9, 10% v/v glycerol, 2 mM $MgCl_2$, and 2 mM dithiothreitol) using PD10 columns (Amersham Biosciences). The purity of the isolated proteins was verified by SDS-PAGE, and the protein concentration was determined by Bradford assay.

Example 2

Analysis of Hexanoyl-CoA Synthetase Activity

Hexanoyl-CoA synthetase activity was measured by incubating 0.1 µg of enzyme in a 20 µL reaction mixture containing 50 mM HEPES pH 9, 8 mM ATP, 10 mM $MgCl_2$, 0.5 mM CoA, and 4 mM sodium hexanoate. The reactions were incubated for 10 min at 40° C., terminated with 2 µL of 1 N HCl and stored on ice until analysis.

The reaction mixtures were diluted 1:100 with water and subsequently separated using a Waters Acquity UPLC system fitted with an Acquity UPLC BEH C18 column (1.7 µm particle size, 2.1×50 mm column), and analyzed by MS/MS using a Micromass Quattro Ultima triple-quadrupole mass spectrometer. The solvent system used was buffer A: 5 mM TEA and 3 mM acetic acid in water, and buffer B: 5 mM TEA and 3 mM acetic acid in 95:5 methanol:water. The flow program is shown in Table 4. The mass spectrometer settings were: ESI positive mode, collision energy 27 V, cone 135 V, scanning for 866>359 transitions.

TABLE 4

| Flow Program for Liquid Chromatography | | | |
|---|---|---|---|
| Time (min) | Flow rate (mL/min) | % A | % B |
| 0 | 0.2 | 94.7 | 5.3 |
| 1 | 0.2 | 94.7 | 5.3 |
| 6 | 0.2 | 85.0 | 15.0 |
| 10 | 0.2 | 0.1 | 50.0 |
| 21 | 0.2 | 0.1 | 99.9 |
| 22 | 0.8 | 0.1 | 99.9 |
| 24 | 0.8 | 0.1 | 99.9 |
| 24.1 | 0.4 | 94.7 | 5.3 |
| 27 | 0.4 | 94.7 | 5.3 |
| 27.1 | 0.2 | 94.7 | 5.3 |

As shown in FIG. 2, CsHCS1 and CsHCS2 catalyzed the formation of hexanoyl-CoA from hexanoate and CoA. FIGS. 2A and 2B show the elution of authentic hexanoyl-CoA standard. FIG. 2C shows a complete assay comprising CsHCS1, 50 mM HEPES pH 9, 8 mM ATP, 10 mM $MgCl_2$, 0.5 mM CoA, and 4 mM sodium hexanoate. A compound with the same mass transitions and elution time as the authentic hexanoyl-CoA standard can be seen at 9.25 minutes. FIG. 2D shows a complete assay comprising of CsHCS2, 50 mM HEPES pH 9, 8 mM ATP, 10 mM $MgCl_2$, 0.5 mM CoA, and 4 mM sodium hexanoate. A compound with the same mass transitions and elution time as the authentic hexanoyl-CoA standard can be seen at 9.25 minutes. FIGS. 2E and 2F show negative controls with inactivated (boiled) CsHCS1 and CsHCS2 enzymes. As can be seen in FIGS. 2E and 2F, these assays showed no hexanoyl-CoA synthesis.

Both CsHCS1 and CsHCS2 exhibited temperature and pH optima of 40° C. and pH 9, respectively. In testing a range of divalent cations, CsHCS1 optimally used $Mg^{2+}$ and to a lesser extent $Mn^{2+}$ and $Co^{2+}$. CsHCS2 activity was highest using $Co^{2+}$, but was also observed to be high with $Mg^{2+}$, $Mn^{2+}$, and to a lesser extent $Ca^{2+}$. The biological relevance of the high activity with $Co^{2+}$ is not clear and $Mg^{2+}$ was used for all further assays.

With hexanoate, CsHCS1 had a $K_m$ of 6.1±1.0 mM, a $V_{max}$ of 15.6±1.7 pKat and a $k_{cat}$ of 4.5 $sec^{-1}$. CsHCS2 had a $K_m$ of 320 nM, a $V_{max}$ of 1.7 pKat, and a $k_{cat}$ of 57.6 $sec^{-1}$.

Example 3

Testing with Different Carboxylic Acids

To test the range of carboxylic acids that CsHCS1 and CsHCS2 can activate, enzyme assays were performed with a broad range of carboxylic acids and limiting ATP. The assay conditions used were similar to Schneider K et al. (2005). A new type of peroxisomal acyl-coenzyme A synthetase from *Arabidopsis thaliana* has the catalytic capacity to activate biosynthetic precursors of jasmonic acid. *The Journal of Biological Chemistry*, 280:13962-72. Briefly, purified HCS enzyme (1 μg) was incubated with 500 μM carboxylic acid substrate and 100 μM CoA in an assay containing 100 mM HEPES pH 9, 250 μM $MgCl_2$, 50 μM ATP and 1 mM DTT. All carboxylic acid substrates were dissolved in 2% v/v Triton™ X-100, leading to a final concentration 0.05% Triton X-100 in the assay. After reacting for 3 h at 29° C., 10 μL aliquots of the reactions were transferred to 96-well plates for a luciferin/luciferase based measurement of unconsumed ATP. The plates were analyzed with a 1420 Multilabel counter (PerkinElmer). To each well, 90 μL of a solution containing 100 mM Tris pH 7.8, 1 mM $MgCl_2$, 2.3 μg luciferin, and 0.5 μg of luciferase was injected, and after shaking for 2 seconds the luminescence was measured for 15 seconds without a filter in place. Lower readings, compared to the reactions with no carboxylic acid substrate, indicate a higher amount of enzymatic activity and therefore substrate utilization. The results are shown in FIG. 3, wherein error bars represent the percent error of the ratio, n=3.

Figure 3A:
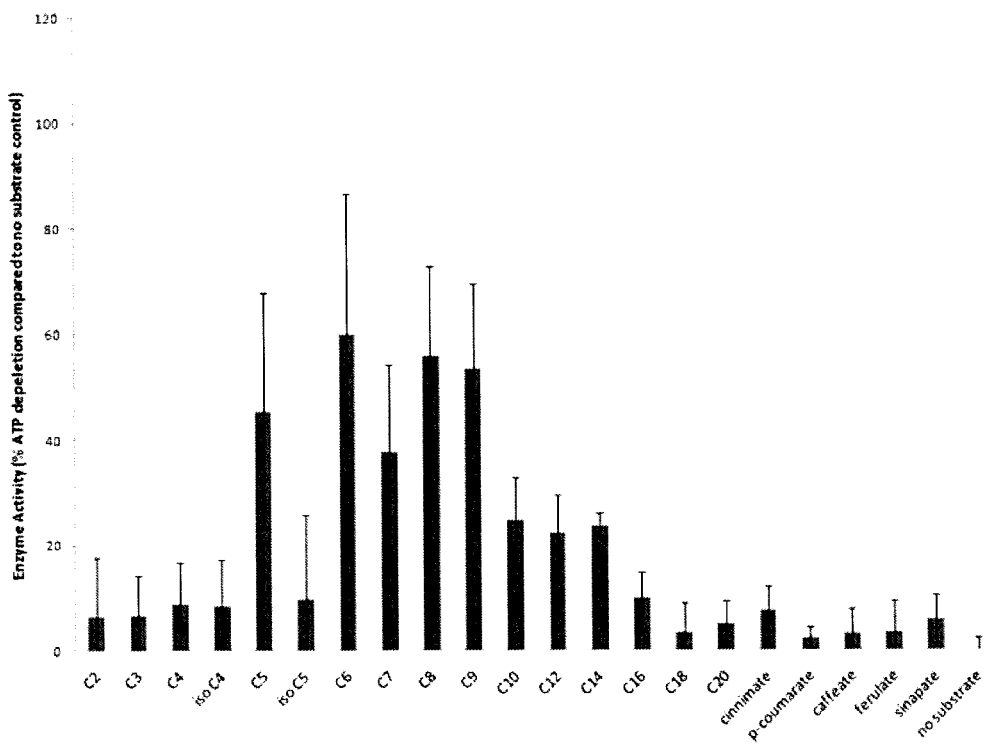
FIG. 3A depicts carboxylic acid substrates utilized by CsHCS1.
Figure 3B:
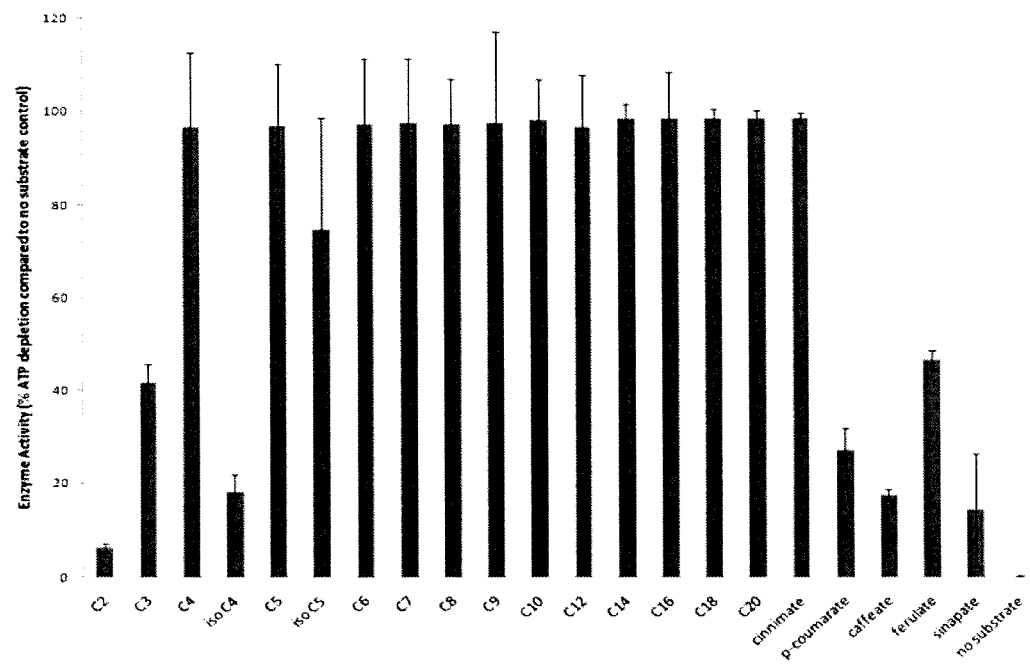
FIG. 3B depicts carboxylic acid substrates utilized by CsHCS2.

As is shown in FIG. 3A, CsHCS1 was observed to utilize hexanoate (six carbons), octanoate (eight carbons), and nonanoate (nine carbons), and to a lesser extent valerate (five carbons) and heptanoate (seven carbons), as substrates. In contrast, as is shown in FIG. 3B, CsHCS2 exhibited greater promiscuity, and is able to utilize a broad range of substrates, ranging from propanoate (C3) to arachidoate (C20), and a number of phenylpropanoids (cinnamate, ferulate, and to a lesser extent p-coumarate).

In a separate experiment, the kinetic properties of CsHCS1 and CsHCS3 were more accurately measured for CoA and representative short (butanoate), medium (hexanoate and decanoate), and long-chain (palmitate) fatty acids (Table 5). High CoA concentrations inhibited CsHCS1. Using a non-linear regression substrate inhibition model, the $K_i$ of CsHCS1 was estimated to be 5.101±1.8 mM. CoA did not inhibit CsHCS2 at the concentrations tested. Decanoic acid inhibited CsHCS2 ($K_i$=120.8±47.9 μM) and slightly inhibited CsHCS1 in concentrations above 4 mM (K not measured). These data show the same trends as the kinetic data presented above.

TABLE 5

Kinetic properties of CsHCS1 and CsHCS2.

| | CsHCS1 | | CsHCS2 | | |
|---|---|---|---|---|---|
| Substrate | $K_m$ | $V_{max}$ (pKat) | $K_m$ | $V_{max}$ (pKat) | $k_{cat}$ ($s^{-1}$) |
| CoA | 0.26 ± 0.05 μM | — | 0.16 ± 0.01 μM | — | — |
| butanoate | >10 mM | — | >10 mM | — | — |
| hexanoate | 3.7 ± 0.7 mM | 6.8 ± 0.7 | 261 ± 37 μM | 1.8 ± 0.05 | 57.6 |
| decanoate | 1.7 ± 0.2 mM | 1.8 ± 0.7 | 16.1 ± 5.8 μM | 1.6 ± 0.1 | 10.0 |
| palmitate | n.d.[a] | — | 1.3 ± 0.5 μM | 0.4 ± 0.01 | 2.4 |

[a] not determined due to lack of catalytic activity

Example 4

Synthesis of Olivetolic Acid using CsHCS2

CsHCS2 was used for the chemoenzymatic synthesis of the aromatic polyketide olivetolic acid. Olivetolic acid is the first committed precursor for cannabinoid biosynthesis. This in vitro synthesis made use of four recombinant enzymes: CsHCS2, malonyl-CoA synthetase (MCS) from *Rhizobium leguminosarum*, "olivetol synthase"/polyketide synthase from *cannabis*, and olivetolic acid synthase from *cannabis*.

Malonyl-CoA synthetase (MCS) was amplified from genomic DNA of *Rhizobium leguminosarum* with the primers MCS forward and MCS reverse (see Table 3). The PCR product was cloned into pCR8/GW/TOPO vector (Invitrogen) recombined into pHIS8/GW vector. After verification by sequencing, the plasmid was transformed into the *E. coli* Rosetta II (DE3). Recombinant MCS was expressed and purified as described for the CsHCS enzymes.

The cloning, expression and purification of "olivetol synthase"/polyketide synthase and olivetolic acid synthase were done as follows. For expression in *E. coli* cells, the open reading frames of polyketide synthase/olivetol synthase and olivetolic acid synthase were amplified by PCR, cloned into pHIS8/GW for polyketide synthase/olivetol synthase or pET100 (Invitrogen) for olivetolic acid synthase and transformed into *E. coli* BL21 (DE3) (Invitrogen). Cloning was verified by sequencing.

Olivetolic acid synthase was expressed in 200 mL terrific broth culture while polyketide synthase/olivetol synthase grown in a 1 L culture. Both cultures were incubated at 30° C./150 rpm shaking, induced with 0.5 μM IPTG and grown overnight. The cultures were centrifuged at 16,000 g for 20 min, and the pellets lysed by treatment with lysozyme and sonication. The cleared lysates were mixed with Talon resin (200 μL for olivetolic acid synthase, 1 mL for polyketide synthase/olivetol synthase; Clontech), washed with 5 mL of His-tag Wash Buffer (50 mM Tris-HCl (pH 7), 150 mM NaCl, 20 mM imidazole, 10 mM β-mercaptoethanol) and the recombinant proteins eluted using His-tag Elution Buffer (20 mM Tris HCl (pH 7), 150 mM NaCl, 100 mM imidazole, 10 mM β-mercaptoethanol). The eluate was concentrated using a YM10 concentrator and the buffer exchanged to Storage Buffer (20 mM HEPES (pH 7.5), 25 mM NaCl, 10% glycerol, 5 mM DTT). The final protein solutions were quantified by using an RC/DC protein assay kit (Bio-Rad) which found protein concentrations of 0.5 mg/mL (olivetolic acid synthase) and 5.6 mg/mL (polyketide synthase/olivetol synthase). SDS-PAGE gel analysis confirmed the purity of both proteins.

Figure 4:
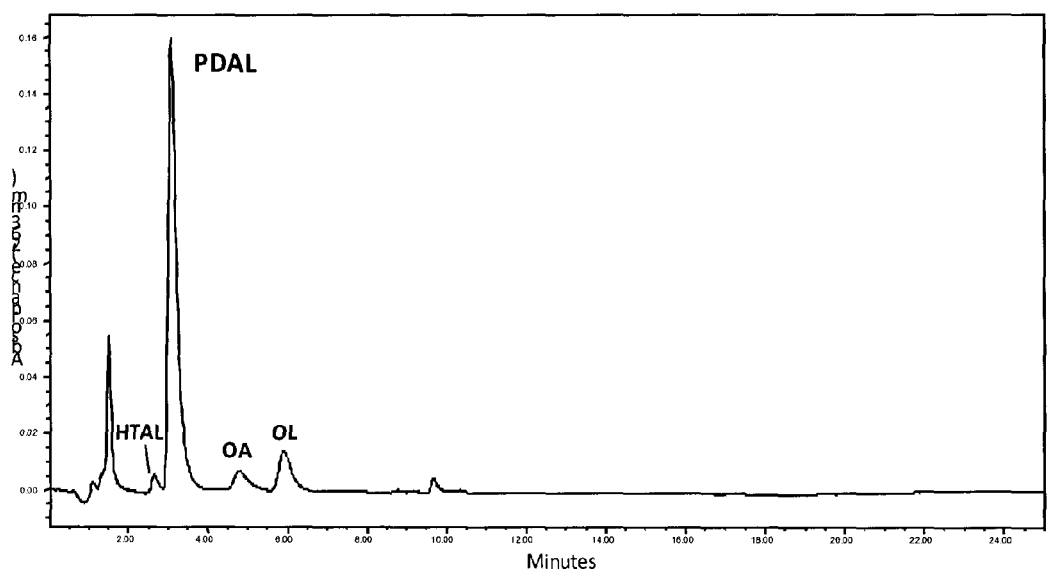
FIG. 4 depicts a high performance liquid chromatography analysis of the products produced by a coupled enzymatic assay consisting of the *Cannabis sativa* hexanoyl-CoA synthetase CsHCS2, malonyl-CoA synthetase (MCS), *Cannabis sativa* "olivetol synthase"/polyketide synthase, and *Cannabis sativa* olivetolic acid synthase. Eluted compounds were detected by absorbance at 263 nm and identified both by having the same retention times as isolated standards, and by their mass using a single quadrapole mass detector. The detection of olivetol and olivetolic acid indicates that CsHCS2 is capable of providing sufficient hexanoyl-CoA substrate for the synthesis of olivetolic acid. Assays lacking CsHCS2, CoA, or hexanoate did not produce any polyketide products. HTAL=hexanoyltriacetic lactone, PDAL=pentyldiacetic lactone, OA=olivetolic acid, OL=olivetol.

The ability to couple hexanoyl-CoA synthesis with aromatic polyketide synthesis using inexpensive reagents was tested by performing enzyme assays consisting of 4 mM hexanoate, 8 mM malonate, 0.4 mM CoA, 0.4 mM ATP, 5 mM $MgCl_2$, 2 mM DTT, 20 mM HEPES pH 7.5, 0.3 μg CsHCS2, 12 μg MCS, 8 μg "olivetol synthase"/PKS and 10 μg OAS. The reaction was incubated at room temperature for 16 h, acidified and extracted in ethyl acetate. The polar fraction was recovered, evaporated to dryness and resuspended in 50 μL of methanol. An aliquot (5 μL) was analyzed by LCMS, and products were identified by their retention times and masses (see FIG. 4).

Example 5

Synthesis of Olivetolic Acid in Yeast Using CsHCS1 and CsHCS2

Yeast (Saccharomyces cerevisiae) was engineered to produce olivetolic acid by using CsHCS1 and CsHCS2 to synthesize hexanoyl-CoA, and a fusion of the cannabis "olivetol synthase"/polyketide synthase (PKS) and olivetolic acid synthase (OAS) to form olivetolic acid.

OAS was cloned in frame with the "olivetol synthase"/PKS using a synthetic linker sequence encoding the amino acids AATSGSTGSTGSTGSGRSTGSTGSTGSGRSHMV (SEQ ID NO: 11) in the pESC-Trp yeast expression vector (Stratagene) under control of the GAL10 promoter. The open reading frame of CsHCS1 was cloned into the yeast expression vector pYESDEST52-Ura (Invitrogen) using Gateway technology. The open reading frame of CsHCS2 was cloned into pESC-Trp yeast expression vector (Stratagene) under control of the GAL1 promoter.

Figure 5:
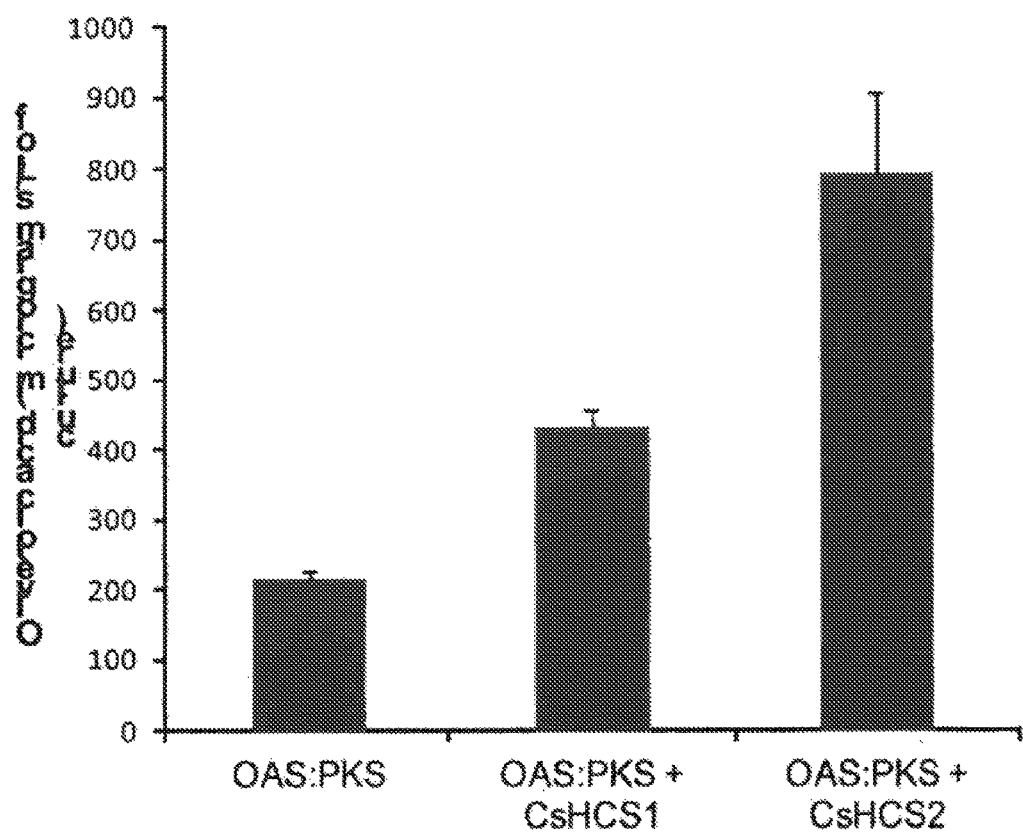
FIG. 5 depicts a graph showing olivetolic acid production in yeast cells engineered to produce olivetolic acid by using CsHCS1 and CsHCS2 to synthesize hexanoyl-CoA, and a fusion of the *cannabis* "olivetol synthase"/polyketide synthase (PKS) and olivetolic acid synthase (OAS) to form olivetolic acid.

Yeast cells (InVSc I, Invitrogen) were transformed with the above constructs (OAS:"olivetol synthase"/PKS fusion alone, OAS:"olivetol synthase"/PKS fusion and CsHCS1; OAS:"olivetol synthase"/PKS fusion and CsHCS2) and the transformants grown on a SD-Trp plate for 3 days at 28° C. For each, a single colony was inoculated into 3 mL of SD-Trp glucose medium and incubated with shaking at 28° C. for 2 days. A 0.5 mL aliquot of starter culture was used to inoculate 10 mL of SD-Trp galactose medium containing 1 mM sodium hexanoate and incubated at 20° C. for 4 days. The complete culture was extracted with ethyl acetate, dried and the residue resuspended in 100 μL of 30% acetonitrile/70% water/0.05% formic acid. The products were analyzed using LCMS (see FIG. 5).

Example 6

Role of CsHSC1 and CsHSC2 in Cannabinoid Biosynthesis in Plants

Through a sequence-based analysis of the trichome EST dataset and biochemical assay of five AAEs, two that possess hexanoyl-CoA synthetase activity were identified (CsHSC1 and CsHSC2). To determine which of these is likely to be involved in the cannabinoid biosynthetic pathway, qRT-PCR and sub-cellular localization experiments were performed.

qRT-PCR of CsHSC1 and CsHSC2 Expression

'Finola' plants were grown from seed until mid-flowering stage. Roots, stems, leaves, female flowers (with trichomes and after trichome isolation using the Beadbeater), trichome cells and male flowers were sampled from three plants. Total RNA was isolated as described above. RNA had an $Abs_{260}$:$Abs_{280}$ of >1.9 and showed distinct ribosomal bands on denaturing gel. First-strand cDNA were synthesized using 0.5 μg RNA with a QuantiTect cDNA Synthesis kit (Qiagen). Each 20 μL cDNA sample was diluted 1:4 with water, and 1 μL used as a PCR template. Gene-specific primers were designed to produce amplicons of 90-200 bp. PCR reactions (20 μL) were performed in 96-well plates using a SYBR Green based assay (QuantiFast SYBR Green kit, Qiagen) with a StepOne Plus instrument (Applied Biosystems). The cycling parameters used were 95° C. for 5 min followed by 40 cycles of 95° C. for 10 s, 60° C. for 30 s, and a standard dissociation protocol (95° C. 15 s, 60° C. for 1 min, 60-95° C. in 0.3° C. increments for 15 s). Experiments were performed using cDNAs from three plants with two technical replicates. Actin, which was found to have stable expression in all tissues tested, was used as a reference gene. The efficiencies for all primer pairs were 90-110% as calculated using the standard curve method. $C_t$ values were calculated using StepOne Software (Applied Biosystems). The $2^{-\Delta\Delta Ct}$ method was used for relative gene expression analysis.

Subcellular Localization of CsHSC1 and CsHSC2

YFP:CsHSC1 and YFP:CsHSC2 fusions were constructed by recombination into pEARLYGATE104 (Earley, K. W., Haag, J. R., Pontes, O., Opper, K., Juehne, T., Song, K. and Pikaard, C. S. (2006). Gateway-compatible vectors for plant functional genomics and proteomics. Plant J. 45, 616-629.) using LR recombinase (Invitrogen). To generate an OLS:CFP construct, OLS lacking a stop codon was cloned into pCR8/GW/TOPO before recombination into pEARLYGATE102 using LR recombinase. The peroxisome marker PX-CK (Nelson, B. K., Cai, X. and Nebenführ, A. (2007). A multicolored set of in vivo organelle markers for co-localization studies in Arabidopsis and other plants. Plant J. 51, 1126-1136.) was from ABRC (www.arabidopsis.org). Plasmids were transformed into Agrobacterium tumefaciens GV3101 by electroporation and selected on LB plates containing 10 μg/mL rifampacin and 50 μg/mL kanamycin. Leaves of two-week old Nicotiana benthamiana plants were infiltrated with the Agrobacterium solution at an $OD_{600}$ of 0.02 (Sparkes, I. A., Runions, J., Kearns, A. and Hawes, C. (2006). Rapid, transient expression of fluorescent fusion proteins in tobacco plants and generation of stably transformed plants. Nat. Protocol. 1, 2019-2025.). Two days post-infiltration, leaf epidermal cells were visualized using a Zeiss LSM510 confocal microscope. CFP was visualized with excitation 458 nm and image collection with a 475-525 nm bandpass filter; YFP at 514 nm with a 530-600 nm bandpass filter. Images were collected and analyzed using the Zeiss LSM software package.

Figure 6:
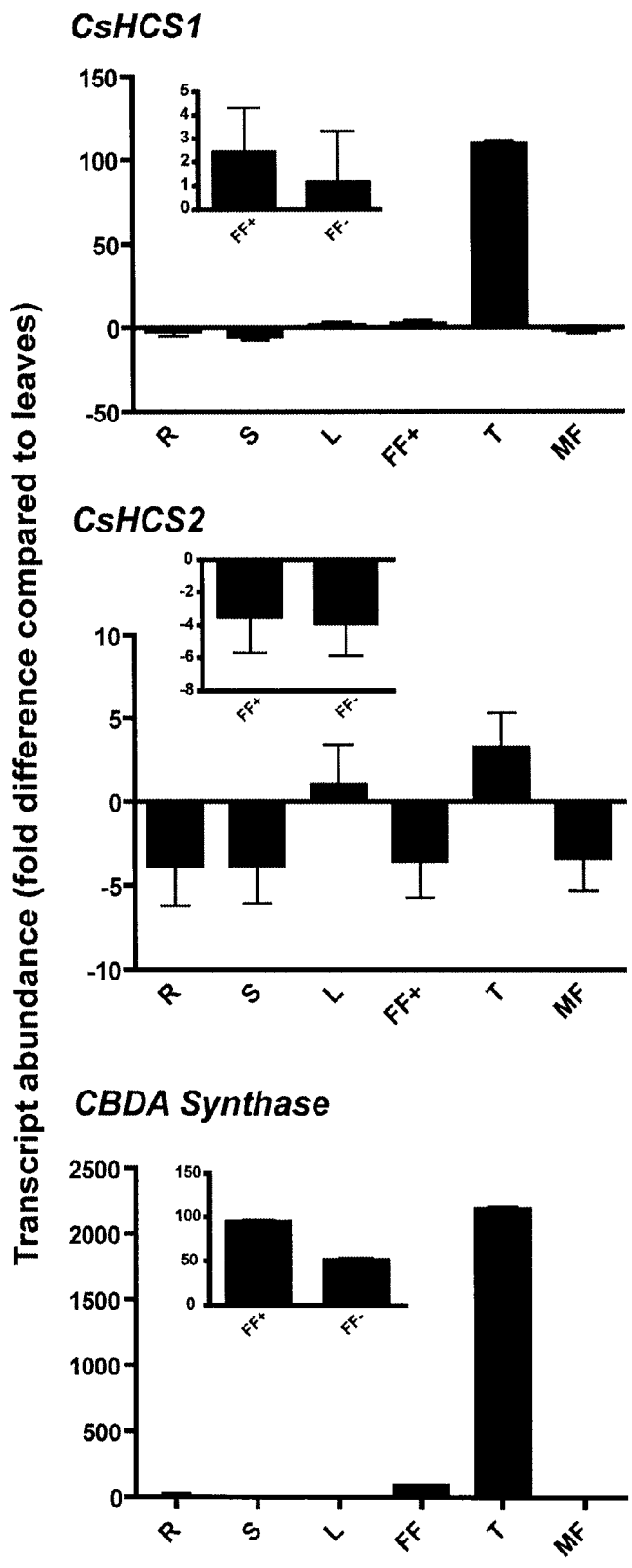
FIG. 6 depicts qRT-PCR analysis of CsHCS1, CsHCS2 and CBDA Synthase expression in different tissues of the hemp cultivar 'Finola'. Gene expression values relative to actin were plotted as fold differences compared to leaves, with leaf expression assigned a value of 1. Insets depict gene expression in female flowers with and without trichomes, with values also indicated as fold differences compared to leaves. R, roots; S, stems; L, leaves; FF+, female flowers with trichomes; FF−, female flowers with trichomes

The data provides evidence that CsHSC1 is the enzyme involved in cannabinoid biosynthesis. CsHSC1 was the most abundant transcript in the EST catalog, and qRT-PCR data shows that its expression is over 100-fold higher in trichome cells compared to other tissues (FIG. 6). Furthermore, CsHSC1 is localized to the cytosol as evidenced by the sub-cellular localization experiment, which is the same compartment where the putative cannabinoid enzyme OLS is localized. The substrate preference of CsHSC1 provides additional evidence for its role in cannabinoid biosynthesis since it shows more specificity for hexanoate and other short-chain fatty acyl CoAs than CsHSC2 (FIG. 3).

Although CsHSC1 is the enzyme likely involved in cannabinoid biosynthesis in plants, CsHSC2 is more efficient than CsHSC1 at synthesizing hexanoyl-CoA. However, CsHSC2 is localized to the peroxisome and it is not clear how hexanoyl-CoA formed in this compartment could be exported to the cytoplasm where the polyketide synthesis phase of the cannabinoid pathway is located. CsHSC2 accepts a very broad range of substrates, indicating that it is a more generalized acyl-CoA synthetase that may function in peroxisomal β-oxidation.

Both CsHSC1 and CsHSC2 are valuable industrial tools. Knocking out CsHSC1 in *cannabis* plants could lead to a major reduction in cannabinoid levels in the plant, which is very desirable for hemp breeders. Over-expression of CsHSC1 in *cannabis* could lead to elevated cannabinoid levels, which is useful for pharmaceutical purposes. On the other hand, CsHSC2 would be particular useful in reconstituting cannabinoid formation in microorganisms or in an in vitro system.

Example 7

Generation of Mutants in the CsHSC1 and CsHSC2 Genes Using Targeted Induced Local Lesions IN Genomes (TILLING)

Identification of *cannabis* plants with mutations in the CsHSC1 or CsHCS2 genes can be accomplished using TILLING. A mutagenized population of *cannabis* plants is screened using oligonucleotide primers and PCR in order to amplify the genes of interest. Amplified mutant genes are annealed to wild-type genes to find mismatches between the mutant genes and the wild-type genes. Detected differences are used to identify plants that contain mutations in one of both of the CsHSC1 or CsHCS2 genes. Plants containing mutations that lead to altered amino acids in positions that are essential for the stability or alkanoyl-CoA synthetase activity of CsHSC1 or CsHCS2 proteins are unable to produce alkanoyl-CoA precursors for cannabinoid biosynthesis. The resulting plants contain reduced or altered levels cannabinoid products.

The present invention provides genes which encode two alkanoyl CoA synthetase enzymes from *cannabis*. These genes could be used to create, through breeding, targeted mutagenesis or genetic engineering, *cannabis* plants with enhanced cannabinoid production. In addition, inactivating or silencing a gene of the invention in *cannabis* could be used to block cannabinoid biosynthesis and thereby reduce production of cannabinoids such as THCA, the precursor of THC, in *cannabis* plants (e.g. industrial hemp). The genes of the present invention could be used, in combination with genes encoding other enzymes in the cannabinoid pathway, to engineer cannabinoid biosynthesis in other plants or in microorganisms or in cell-free systems, or to produce analogs of cannabinoid compounds or analogs of cannabinoid precursors.

Throughout the present disclosure, reference is made to publications, contents of the entirety of each of which are incorporated by this reference.

Other advantages that are inherent to the invention are obvious to one skilled in the art. The embodiments are described herein illustratively and are not meant to limit the scope of the invention as claimed. Variations of the foregoing embodiments will be evident to a person of ordinary skill and are intended by the inventors to be encompassed by the following claims.

The invention claimed is:

1. A process of decreasing levels of a cannabinoid compound in a *cannabis* plant, *cannabis* cell or *cannabis* tissue, the process comprising using a RNAi nucleic acid molecule comprising a nucleotide sequence complementary to a portion of SEQ ID NO: 1 or SEQ ID NO: 3, to silence in the *cannabis* plant, *cannabis* cell or *cannabis* tissue a gene that encodes an enzyme that catalyzes synthesis of an alkanoyl-CoA, in comparison to a similar variety of organism, cell or tissue grown under similar conditions but without the use of the nucleic acid molecule for silencing.

2. The process of claim 1, wherein the cannabinoid compound is one or more of cannabigerolic acid, $\Delta^9$-tetrahydrocannabinolic acid, cannabidiolic acid, cannabichromenic acid, $\Delta^9$-tetrahydrocannabinol, cannabidiol or cannabichromene or an analog thereof comprising a sidechain of 1 to 9 carbon atoms in length.

3. The process of claim 1, wherein the nucleotide sequence is complementary to a portion of SEQ ID NO:1.

4. The process of claim 1, wherein the nucleotide sequence is complementary to a portion of SEQ ID NO: 3.

5. The process of claim 2, wherein the nucleotide sequence is complementary to a portion of SEQ ID NO: 1.

6. The process of claim 2, wherein the nucleotide sequence is complementary to a portion of SEQ ID NO: 3.

7. The process of claim 1, wherein the use of the nucleic acid molecule comprises a method selected from RNAi, amiRNA, VIGS virus, antisense oligonucleotide, targeted mutagenesis and Targeting Induced Local Lesions IN Genomes (TILLING).

8. The process of claim 1, wherein the enzyme is hexanoyl-CoA synthetase.

9. The process of claim 2, wherein the enzyme is hexanoyl-CoA synthetase.

10. The process of claim 1, wherein the alkanoyl-CoA is hexanoyl-CoA.

11. The process of claim 1, wherein the nucleotide sequence has a length of at least 300 base pairs.

\* \* \* \* \*

SEQUENCE LISTING

<160> NUMBER OF SEQ ID NOS: 11

<210> SEQ ID NO 1
<211> LENGTH: 2163
<212> TYPE: DNA
<213> ORGANISM: Cannabis sativa

<400> SEQUENCE: 1

```
atgggtaaga attacaagtc cctggactct gttgtggcct ctgacttcat agccctaggt      60
atcacctctg aagttgctga gacactccat ggtagactgg ccgagatcgt gtgtaattat     120
ggcgctgcca ctccccaaac atggatcaat attgccaacc atattctgtc gcctgacctc     180
cccttctccc tgcaccagat gctcttctat ggttgctata aagactttgg acctgcccct     240
cctgcttgga tacccgaccc ggagaaagta aagtccacca atctgggcgc acttttggag     300
aagcgaggaa aagagttttt gggagtcaag tataaggatc ccatttcaag cttttctcat     360
ttccaagaat tttctgtaag aaaccctgag gtgtattgga gaacagtact aatggatgag     420
atgaagataa gttttcaaa ggatccagaa tgtatattgc gtagagatga tattaataat     480 ccaggggta gtgaatggct tccaggaggt tatcttaact cagcaaagaa ttgcttgaat     540
gtaaatagta acaagaaatt gaatgataca atgattgtat ggcgtgatga aggaaatgat     600
gatttgcctc taaacaaatt gacacttgac caattgcgta aacgtgtttg gttagttggt     660
tatgcacttg aagaaatggg tttggagaag ggttgtgcaa ttgcaattga tatgccaatg     720
```

-continued

```
catgtggatg ctgtggttat ctatctagct attgttcttg cgggatatgt agttgtttct     780
attgctgata gttttctgc tcctgaaata tcaacaagac ttcgactatc aaaagcaaaa       840
gccattttta cacaggatca tattattcgt gggaagaagc gtattcctt atacagtaga       900
gttgtggaag ccaagtctcc catggccatt gttattcctt gtagtggctc taatattggt     960
gcagaattgc gtgatggcga tatttcttgg gattactttc tagaaagagc aaaagagttt    1020
aaaaattgtg aatttactgc tagagaacaa ccagttgatg cctatacaaa catcctcttc    1080
tcatctggaa caacagggga gccaaaggca attccatgga ctcaagcaac tcctttaaaa    1140
gcagctgcag atgggtggag ccatttggac attaggaaag gtgatgtcat tgtttggccc    1200
actaatcttg gttggatgat gggtccttgg ctggtctatg cttcactcct taatggggct    1260
tctattgcct tgtataatgg atcaccactt gtttctggct ttgccaaatt tgtgcaggat    1320
gctaaagtaa caatgctagg tgtggtccct agtattgttc gatcatggaa aagtaccaat    1380
tgtgttagtg ctatgattg gtccaccatc cgttgctttt cctcttctgg tgaagcatct     1440
aatgtagatg aatacctatg gttgatgggg agagcaaact acaagcctgt tatcgaaatg    1500
tgtggtggca cagaaattgg tggtgcattt tctgctggct cttcttaca agctcaatca    1560
ttatcttcat ttagttcaca atgtatgggt tgcactttat acatacttga caagaatggt    1620
tatccaatgc ctaaaaacaa accaggaatt ggtgaattag cgcttggtcc agtcatgttt    1680
ggagcatcga agactctgtt gaatggtaat caccatgatg tttattttaa gggaatgcct    1740
acattgaatg gagaggtttt aaggaggcat ggggacattt ttgagcttac atctaatggt    1800
tattatcatg cacatggtcg tgcagatgat acaatgaata ttggaggcat caagattagt    1860
tccatagaga ttgaacgagt ttgtaatgaa gttgatgaca gagttttcga cacaactgct    1920
attggagtgc caccttggg cggtggacct gagcaattag taattttctt tgtattaaaa    1980
gattcaaatg atacaactat tgacttaaat caattgaggt tatctttcaa cttgggttta    2040
cagaagaaac taaatcctct gttcaaggtc actcgtgttg tgcctctttc atcacttccg    2100
agaacagcaa ccaacaagat catgagaagg gttttgcgcc agcaattttc tcactttgaa    2160
tga                                                                   2163
```

<210> SEQ ID NO 2
<211> LENGTH: 719
<212> TYPE: PRT
<213> ORGANISM: Cannabis sativa

<400> SEQUENCE: 2

```
Met Gly Lys Asn Tyr Lys Ser Leu Asp Ser Val Val Ala Ser Asp Phe
1               5                   10                  15

Ile Ala Leu Gly Ile Thr Ser Glu Val Ala Glu Thr Leu His Gly Arg
            20                  25                  30

Leu Ala Glu Ile Val Cys Asn Tyr Gly Ala Ala Thr Pro Gln Thr Trp
        35                  40                  45

Ile Asn Ile Ala Asn His Ile Leu Ser Pro Asp Leu Pro Phe Ser Leu
    50                  55                  60

His Gln Met Leu Phe Tyr Gly Cys Tyr Lys Asp Phe Gly Pro Ala Pro
65                  70                  75                  80

Pro Ala Trp Ile Pro Asp Pro Glu Lys Val Lys Ser Thr Asn Leu Gly
                85                  90                  95

Ala Leu Leu Glu Lys Arg Gly Lys Glu Phe Leu Gly Val Lys Tyr Lys
            100                 105                 110
```

```
Asp Pro Ile Ser Ser Phe Ser His Phe Gln Glu Phe Ser Val Arg Asn
            115                 120                 125

Pro Glu Val Tyr Trp Arg Thr Val Leu Met Asp Glu Met Lys Ile Ser
    130                 135                 140

Phe Ser Lys Asp Pro Glu Cys Ile Leu Arg Arg Asp Ile Asn Asn
145                 150                 155                 160

Pro Gly Gly Ser Glu Trp Leu Pro Gly Gly Tyr Leu Asn Ser Ala Lys
                165                 170                 175

Asn Cys Leu Asn Val Asn Ser Asn Lys Lys Leu Asn Asp Thr Met Ile
                180                 185                 190

Val Trp Arg Asp Glu Gly Asn Asp Asp Leu Pro Leu Asn Lys Leu Thr
            195                 200                 205

Leu Asp Gln Leu Arg Lys Arg Val Trp Leu Val Gly Tyr Ala Leu Glu
    210                 215                 220

Glu Met Gly Leu Glu Lys Gly Cys Ala Ile Ala Ile Asp Met Pro Met
225                 230                 235                 240

His Val Asp Ala Val Val Ile Tyr Leu Ala Ile Val Leu Ala Gly Tyr
                245                 250                 255

Val Val Val Ser Ile Ala Asp Ser Phe Ser Ala Pro Glu Ile Ser Thr
            260                 265                 270

Arg Leu Arg Leu Ser Lys Ala Lys Ala Ile Phe Thr Gln Asp His Ile
    275                 280                 285

Ile Arg Gly Lys Lys Arg Ile Pro Leu Tyr Ser Arg Val Val Glu Ala
    290                 295                 300

Lys Ser Pro Met Ala Ile Val Ile Pro Cys Ser Gly Ser Asn Ile Gly
305                 310                 315                 320

Ala Glu Leu Arg Asp Gly Asp Ile Ser Trp Asp Tyr Phe Leu Glu Arg
                325                 330                 335

Ala Lys Glu Phe Lys Asn Cys Glu Phe Thr Ala Arg Glu Gln Pro Val
                340                 345                 350

Asp Ala Tyr Thr Asn Ile Leu Phe Ser Ser Gly Thr Thr Gly Glu Pro
            355                 360                 365

Lys Ala Ile Pro Trp Thr Gln Ala Thr Pro Leu Lys Ala Ala Ala Asp
    370                 375                 380

Gly Trp Ser His Leu Asp Ile Arg Lys Gly Asp Val Ile Val Trp Pro
385                 390                 395                 400

Thr Asn Leu Gly Trp Met Met Gly Pro Trp Leu Val Tyr Ala Ser Leu
                405                 410                 415

Leu Asn Gly Ala Ser Ile Ala Leu Tyr Asn Gly Ser Pro Leu Val Ser
                420                 425                 430

Gly Phe Ala Lys Phe Val Gln Asp Ala Lys Val Thr Met Leu Gly Val
            435                 440                 445

Val Pro Ser Ile Val Arg Ser Trp Lys Ser Thr Asn Cys Val Ser Gly
    450                 455                 460

Tyr Asp Trp Ser Thr Ile Arg Cys Phe Ser Ser Gly Glu Ala Ser
465                 470                 475                 480

Asn Val Asp Glu Tyr Leu Trp Leu Met Gly Arg Ala Asn Tyr Lys Pro
                485                 490                 495

Val Ile Glu Met Cys Gly Gly Thr Glu Ile Gly Gly Ala Phe Ser Ala
            500                 505                 510

Gly Ser Phe Leu Gln Ala Gln Ser Leu Ser Ser Phe Ser Ser Gln Cys
    515                 520                 525
```

```
Met Gly Cys Thr Leu Tyr Ile Leu Asp Lys Asn Gly Tyr Pro Met Pro
            530                 535                 540

Lys Asn Lys Pro Gly Ile Gly Glu Leu Ala Leu Gly Pro Val Met Phe
545                 550                 555                 560

Gly Ala Ser Lys Thr Leu Leu Asn Gly Asn His His Asp Val Tyr Phe
                565                 570                 575

Lys Gly Met Pro Thr Leu Asn Gly Glu Val Leu Arg Arg His Gly Asp
            580                 585                 590

Ile Phe Glu Leu Thr Ser Asn Gly Tyr Tyr His Ala His Gly Arg Ala
        595                 600                 605

Asp Asp Thr Met Asn Ile Gly Gly Ile Lys Ile Ser Ser Ile Glu Ile
610                 615                 620

Glu Arg Val Cys Asn Glu Val Asp Asp Arg Val Phe Glu Thr Thr Ala
625                 630                 635                 640

Ile Gly Val Pro Pro Leu Gly Gly Gly Pro Glu Gln Leu Val Ile Phe
                645                 650                 655

Phe Val Leu Lys Asp Ser Asn Asp Thr Thr Ile Asp Leu Asn Gln Leu
            660                 665                 670

Arg Leu Ser Phe Asn Leu Gly Leu Gln Lys Lys Leu Asn Pro Leu Phe
        675                 680                 685

Lys Val Thr Arg Val Val Pro Leu Ser Ser Leu Pro Arg Thr Ala Thr
690                 695                 700

Asn Lys Ile Met Arg Arg Val Leu Arg Gln Phe Ser His Phe Glu
705                 710                 715

<210> SEQ ID NO 3
<211> LENGTH: 1547
<212> TYPE: DNA
<213> ORGANISM: Cannabis sativa

<400> SEQUENCE: 3
atggagaaat cttttcaga aactcatctt catacccaca aaagccagct ctcattgatt      60
ccgaaaccaa ccaaatactc tccttttccc acttcaaatc tacggttatc aaggtctccc     120
atggctttct caatctgggt atcaagaaaa acgacgtcgt tctcatctac gcccctaatt     180
ctatccactt ccctgtttgt ttcctgggaa ttatagcctc tggagccatt gccactacct     240
caaatcctct ctacacagtt tccgagcttt ccaaacaggt caaggattcc aatcccaaac     300
tcattatcac cgttcctcaa ctcttggaaa agtaaaggg tttcaatctc cccacgattc      360
taattggtcc tgattctgaa caagaatctt ctagtgataa agtaatgacc tttaacgatt     420
tggtcaactt aggtgggtcg tctggctcag aatttccaat tgttgatgat tttaagcaga     480
gtgacactgc tgcgctattg tactcatctg gcacaacggg aatgagtaaa ggtgtggttt     540
tgactcacaa aaacttcatt gcctcttctt taatggtgac aatggagcaa gacctagttg     600
gagagatgga taatgtgttt ctatgctttt tgccaatgtt tcatgtattt ggtttggcta     660
tcatcaccta tgctcagttg cagagaggaa acactgttat ttcaatggcg agatttgacc     720
ttgagaagat gttaaaagat gtggaaaagt ataaagttac ccatttgtgg ttgtgcctc      780 ctgtgatact ggctctgagt aagaacagta tggtgaagaa gtttaatctt tcttctataa     840
agtatattgg ctccggtgca gctcctttgg caaagattt aatggaggag tgctctaagg     900
ttgttcctta tggtattgtt gctcagggat atggtatgac agaaacttgt gggattgtat     960
ccatggagga tataagagga ggtaaacgaa atagtggttc agctggaatg ctggcatctg    1020
gagtagaagc ccagatagtt agtgtagata cactgaagcc cttacctcct aatcaattgg    1080
```

-continued

```
gggagatatg ggtgaagggg cctaatatga tgcaaggtta cttcaataac ccacaggcaa    1140
ccaagttgac tatagataag aaaggttggg tacatactgg tgatcttgga tattttgatg    1200
aagatggaca tctttatgtt gttgaccgta taaaagagct catcaaatat aaaggatttc    1260
aggttgctcc tgctgagctt gaaggattgc ttgtttctca ccctgaaata ctcgatgctg    1320
ttgtgattcc atttcctgac gctgaagcgg gtgaagtccc agttgcttat gttgtgcgct    1380
ctcccaacag ttcattaacc gaaaatgatg tgaagaaatt tatcgcgggc caggttgcat    1440
ctttcaaaag attgagaaaa gtaacattta taaacagtgt cccgaaatct gcttcgggga    1500
aaatcctcag aagagaactc attcagaaag tacgctccaa catgtga                 1547
```

<210> SEQ ID NO 4
<211> LENGTH: 543
<212> TYPE: PRT
<213> ORGANISM: Cannabis sativa

<400> SEQUENCE: 4

```
Met Glu Lys Ser Gly Tyr Gly Arg Asp Gly Ile Tyr Arg Ser Leu Arg
1               5                   10                  15

Pro Pro Leu His Leu Pro Asn Asn Asn Leu Ser Met Val Ser Phe
            20                  25                  30

Leu Phe Arg Asn Ser Ser Tyr Pro Gln Lys Pro Ala Leu Ile Asp
        35                  40                  45

Ser Glu Thr Asn Gln Ile Leu Ser Phe Ser His Phe Lys Ser Thr Val
    50                  55                  60

Ile Lys Val Ser His Gly Phe Leu Asn Leu Gly Ile Lys Lys Asn Asp
65                  70                  75                  80

Val Val Leu Ile Tyr Ala Pro Asn Ser Ile His Phe Pro Val Cys Phe
                85                  90                  95

Leu Gly Ile Ile Ala Ser Gly Ala Ile Ala Thr Thr Ser Asn Pro Leu
            100                 105                 110

Tyr Thr Val Ser Glu Leu Ser Lys Gln Val Lys Asp Ser Asn Pro Lys
        115                 120                 125

Leu Ile Ile Thr Val Pro Gln Leu Leu Glu Lys Val Lys Gly Phe Asn
    130                 135                 140

Leu Pro Thr Ile Leu Ile Gly Pro Asp Ser Glu Gln Glu Ser Ser Ser
145                 150                 155                 160

Asp Lys Val Met Thr Phe Asn Asp Leu Val Asn Leu Gly Gly Ser Ser
                165                 170                 175

Gly Ser Glu Phe Pro Ile Val Asp Asp Phe Lys Gln Ser Asp Thr Ala
            180                 185                 190

Ala Leu Leu Tyr Ser Ser Gly Thr Thr Gly Met Ser Lys Gly Val Val
        195                 200                 205

Leu Thr His Lys Asn Phe Ile Ala Ser Ser Leu Met Val Thr Met Glu
    210                 215                 220

Gln Asp Leu Val Gly Glu Met Asp Asn Val Phe Leu Cys Phe Leu Pro
225                 230                 235                 240

Met Phe His Val Phe Gly Leu Ala Ile Ile Thr Tyr Ala Gln Leu Gln
                245                 250                 255

Arg Gly Asn Thr Val Ile Ser Met Ala Arg Phe Asp Leu Glu Lys Met
            260                 265                 270

Leu Lys Asp Val Glu Lys Tyr Lys Val Thr His Leu Trp Val Val Pro
        275                 280                 285
```

```
Pro Val Ile Leu Ala Leu Ser Lys Asn Ser Met Val Lys Lys Phe Asn
        290                 295                 300

Leu Ser Ser Ile Lys Tyr Ile Gly Ser Gly Ala Ala Pro Leu Gly Lys
305                 310                 315                 320

Asp Leu Met Glu Glu Cys Ser Lys Val Val Pro Tyr Gly Ile Val Ala
                325                 330                 335

Gln Gly Tyr Gly Met Thr Glu Thr Cys Gly Ile Val Ser Met Glu Asp
            340                 345                 350

Ile Arg Gly Gly Lys Arg Asn Ser Gly Ser Ala Gly Met Leu Ala Ser
        355                 360                 365

Gly Val Glu Ala Gln Ile Val Ser Val Asp Thr Leu Lys Pro Leu Pro
370                 375                 380

Pro Asn Gln Leu Gly Glu Ile Trp Val Lys Gly Pro Asn Met Met Gln
385                 390                 395                 400

Gly Tyr Phe Asn Asn Pro Gln Ala Thr Lys Leu Thr Ile Asp Lys Lys
                405                 410                 415

Gly Trp Val His Thr Gly Asp Leu Gly Tyr Phe Asp Glu Asp Gly His
            420                 425                 430

Leu Tyr Val Val Asp Arg Ile Lys Glu Leu Ile Lys Tyr Lys Gly Phe
        435                 440                 445

Gln Val Ala Pro Ala Glu Leu Glu Gly Leu Leu Val Ser His Pro Glu
450                 455                 460

Ile Leu Asp Ala Val Val Ile Pro Phe Pro Asp Ala Glu Ala Gly Glu
465                 470                 475                 480

Val Pro Val Ala Tyr Val Val Arg Ser Pro Asn Ser Ser Leu Thr Glu
                485                 490                 495

Asn Asp Val Lys Lys Phe Ile Ala Gly Gln Val Ala Ser Phe Lys Arg
            500                 505                 510

Leu Arg Lys Val Thr Phe Ile Asn Ser Val Pro Lys Ser Ala Ser Gly
        515                 520                 525

Lys Ile Leu Arg Arg Glu Leu Ile Gln Lys Val Arg Ser Asn Met
530                 535                 540
```

<210> SEQ ID NO 5
<211> LENGTH: 23
<212> TYPE: DNA
<213> ORGANISM: Artificial Sequence
<220> FEATURE:
<223> OTHER INFORMATION: CsHCS1 forward primer

<400> SEQUENCE: 5
atgggtaaga attacaagtc cct                                          23

<210> SEQ ID NO 6
<211> LENGTH: 30
<212> TYPE: DNA
<213> ORGANISM: Artificial Sequence
<220> FEATURE:
<223> OTHER INFORMATION: CsHCS1 reverse primer

<400> SEQUENCE: 6
gagctctcat tcaaagtgag aaaattgctg                                   30

<210> SEQ ID NO 7
<211> LENGTH: 23
<212> TYPE: DNA
<213> ORGANISM: Artificial Sequence
<220> FEATURE:
<223> OTHER INFORMATION: CsHCS2 forward primer

```
<400> SEQUENCE: 7
atggagaaat ctgggtatgg aag                                           23

<210> SEQ ID NO 8
<211> LENGTH: 22
<212> TYPE: DNA
<213> ORGANISM: Artificial Sequence
<220> FEATURE:
<223> OTHER INFORMATION: CsHCS2 reverse primer

<400> SEQUENCE: 8
tcacatgttg gagcgtactt tc                                            22

<210> SEQ ID NO 9
<211> LENGTH: 22
<212> TYPE: DNA
<213> ORGANISM: Artificial Sequence
<220> FEATURE:
<223> OTHER INFORMATION: MCS forward primer

<400> SEQUENCE: 9
atgagcaacc atcttttcga cg                                            22

<210> SEQ ID NO 10
<211> LENGTH: 24
<212> TYPE: DNA
<213> ORGANISM: Artificial Sequence
<220> FEATURE:
<223> OTHER INFORMATION: MCS reverse primer

<400> SEQUENCE: 10
ttacgtcctg gtataaagat cggc                                          24

<210> SEQ ID NO 11
<211> LENGTH: 33
<212> TYPE: PRT
<213> ORGANISM: Artificial Sequence
<220> FEATURE:
<223> OTHER INFORMATION: Synthetic Linker

<400> SEQUENCE: 11

Ala Ala Thr Ser Gly Ser Thr Gly Ser Thr Gly Ser Thr Gly Ser Gly
1               5                   10                  15
Arg Ser Thr Gly Ser Thr Gly Ser Thr Gly Ser Gly Arg Ser His Met
            20                  25                  30
Val
```